US008889122B2

(12) United States Patent
Dinsmore

(10) Patent No.: US 8,889,122 B2
(45) Date of Patent: Nov. 18, 2014

(54) CELLULAR CARDIOMYOPLASTY AS SUPPORTIVE THERAPY IN PATIENTS WITH HEART DISEASE

(75) Inventor: Jonathan H. Dinsmore, Brookline, MA (US)

(73) Assignee: Mytogen, Inc., Marlborough, MA (US)

( * ) Notice: Subject to any disclaimer, the term of this patent is extended or adjusted under 35 U.S.C. 154(b) by 1206 days.

(21) Appl. No.: 11/430,693

(22) Filed: May 9, 2006

(65) Prior Publication Data

US 2006/0276685 A1 Dec. 7, 2006

Related U.S. Application Data

(60) Provisional application No. 60/678,976, filed on May 9, 2005.

(51) Int. Cl.
| | |
|---|---|
| *C12N 5/02* | (2006.01) |
| *A61K 35/28* | (2006.01) |
| *A61K 35/34* | (2006.01) |
| *C12N 5/077* | (2010.01) |
| *A61K 35/54* | (2006.01) |
| *A61K 35/12* | (2006.01) |

(52) U.S. Cl.
CPC ............... *A61K 35/34* (2013.01); *A61K 35/12* (2013.01); *A61K 35/28* (2013.01); *C12N 5/0658* (2013.01); *A61K 35/545* (2013.01)
USPC ....................................................... 424/93.7

(58) Field of Classification Search
None
See application file for complete search history.

(56) References Cited

U.S. PATENT DOCUMENTS

| | | | |
|---|---|---|---|
| 5,130,141 A | 7/1992 | Law et al. | |
| 5,143,842 A | 9/1992 | Ham et al. | |
| 5,199,942 A | 4/1993 | Gillis | |
| 5,324,656 A | 6/1994 | Ham et al. | |
| 5,374,544 A | 12/1994 | Schwartz et al. | |
| 5,405,772 A | 4/1995 | Ponting | |
| 5,538,722 A | 7/1996 | Blau et al. | |
| 5,543,318 A | 8/1996 | Smith et al. | |
| 5,580,779 A | 12/1996 | Smith et al. | |
| 5,602,301 A | 2/1997 | Field | |
| 5,733,727 A | 3/1998 | Field | |
| 5,919,449 A | 7/1999 | Dinsmore | |
| 5,968,983 A | 10/1999 | Kaesemeyer | |
| 5,972,013 A | 10/1999 | Schmidt | |
| 5,985,653 A | 11/1999 | Armstrong et al. | |
| 5,994,129 A | 11/1999 | Armstrong et al. | |
| 6,015,671 A | 1/2000 | Field | |
| 6,096,532 A | 8/2000 | Armstrong et al. | |
| 6,099,832 A | 8/2000 | Mickle et al. | |
| 6,107,034 A | 8/2000 | Wiegel et al. | |
| 6,110,459 A | 8/2000 | Mickle et al. | |
| 6,151,525 A | 11/2000 | Soykan et al. | |
| 6,228,635 B1 | 5/2001 | Armstrong et al. | |
| 6,238,908 B1 | 5/2001 | Armstrong et al. | |
| 6,239,172 B1 | 5/2001 | Kaesemeyer | |
| 6,261,832 B1 | 7/2001 | Law | |
| 6,491,912 B2 | 12/2002 | Dinsmore | |
| 6,673,604 B1 | 1/2004 | Edge | |
| 7,189,391 B2 | 3/2007 | Tremblay | |
| 2001/0053354 A1 | 12/2001 | Dinsmore | |
| 2003/0022367 A1 | 1/2003 | Xu | |
| 2003/0113301 A1 | 6/2003 | Edge et al. | |
| 2003/0232431 A1 | 12/2003 | Law | |
| 2004/0191225 A1 | 9/2004 | Dinsmore et al. | |
| 2007/0178077 A1 | 8/2007 | Tremblay | |

FOREIGN PATENT DOCUMENTS

| | | |
|---|---|---|
| EP | 898967 | 3/1999 |
| EP | 00946713 | 3/2007 |
| WO | WO 90/15863 | 12/1990 |
| WO | WO 95/12979 | 5/1995 |
| WO | WO 95/14079 | 5/1995 |
| WO | WO 96/18303 | 6/1996 |
| WO | WO 96/38543 | 12/1996 |
| WO | WO 98/17784 | 4/1998 |
| WO | WO 98/27995 | 7/1998 |
| WO | WO 98/54301 | 12/1998 |
| WO | WO 99/66036 | 12/1999 |
| WO | WO 00/78119 | 12/2000 |
| WO | WO 01/22978 | 5/2001 |
| WO | WO-2004/014302 | 2/2004 |

OTHER PUBLICATIONS

Aly El-Banayosy et al., "Device and patient management in a bridge-to-transplant setting" Ann Thorac Surg 2001;71:98-102.*
Wayne Richenbacher "Surgery Treatment for End Stage Heart Disease: Frequently Asked Questions" 2000, 4 pages, www.uihealthcare.com/topics/medicaldepartments/surgery/endstageheartdisease/index.html.*
Abercrombie, et al., *Ant. Rec.*, 94:239-247, 1946.

(Continued)

*Primary Examiner* — Allison Fox
(74) *Attorney, Agent, or Firm* — Wolf, Greenfield & Sacks, P.C.

(57) ABSTRACT

The present invention provides a system for treating heart disease as a "bridge to recovery" using cellular cardiomyoplasty. The system is particularly useful in selecting and treating patients with damaged myocardium due coronary artery disease, myocardial infarction, congestive heart failure, and ischemia. Based on various clinical criteria, a patient is selected and optionally treated using cellular cardiomyoplasty to improve the patient's cardiac function. The cardiomyoplasty may be combined with other treatments such as medications or left ventricular assist devices. Preferably, the cellular cardiomyoplasty eliminates the need for invasive surgery such as by-pass grafting or cardiac transplantation. The invention also provides kits for use in selecting and treating patients using the inventive method.

20 Claims, 6 Drawing Sheets

(56) References Cited

OTHER PUBLICATIONS

Anyanwu, et al., *BMJ*, 326:509-510, 2003.
Askari, et al., *JACC*, 43:1908-1914, 2004.
Atkins, et al., *Ann. Thorac, Surg.*, 67:124-129, 1999.
Balsam, et al., *Nature*, 428:668-673, 2004.
Boheler, et al., *Circ. Res.*, 91:189-201, 2002.
Boyle, et al., *Circulation*, 88:2872-2883, 1993.
Brasselet, et al., *J. Am. Coll. Cardiol.*, 41:67A-68A, 2003.
Broomhead, et al., *Br. J. Anseth.*, 78:323-325, 1997.
Chazaud, et al., *Cardiovasc. Res.*, 58:444-450, 2003.
Chedrawy, et al., *J. Thorac. Cardiovasc. Surg.*, 124:584-90, 2002.
Chiu, et al., *Ann. Thor. Surg.*, 60:12-18, 1995.
Dib, et al., *J. Envasc. Ther.*, 9:313-319, 2002.
Dorfman, et al., *J. Thor. Cardiovasc. Surg.*, 116:744-751, 1988.
Gheorghiade, et al., *Circulation*, 97:282-289, 1998.
Ghostine, et al., *Circulation*, 106:131-136, 2002.
Grossman, et al., *Catheterization and Cardiovascular Interventions*, 55:392-397, 2002.
Hagege, et al., *Lancet*, 361:492, 2003.
Havenith, et al., *Histochem.*, 93:497, 1990.
Hon, et al., *Ann. Thorac. Surg.*, 75:S36-41, 2003.
International Search Report, PCT/US06/17683, mailed on Nov. 1, 2007.
Jackson, et al., *J. Clin. Invest.*, 107:1395-1402, 2001.
Jain, et al., *Circulation*, 103:1920-1927, 2001.
Kada, et al., *J. Mol. Cell. Cardiol.*, 31:247-259, 1999.
Kamihata, et al., *Circulation*, 104:1046-1052, 2001.
Kehat, et al., *J. Clin. Invest.*, 108:407-414, 2001.
Kessler, et al., *Annu. Rev. Physiol.*, 61:219-242, 1999.
Kherani, et al., *Cardiology*, 101:93-103, 2004.
Klug, et al., *J. Clin. Invest.*, 98:216-224, 1996.
Kocher, et al., *Nature Medicine*, 7:430-436, 2001.
Koh, et al., *J. Clin. Invest.*, 96:2034-2042, 1995.
Kornowski, et al., *Circulation*, 98:1116-1124, 1998.
Leor, et al., *Circulation*, Nov. 7, 2000;102(19 Suppl 3):III56-61.
Li, et al., *Ann. Thorac. Surg.*, 62:654-661, 1996.
Li, et al., *Circulation*, Nov. 4, 1997;96(9 Suppl):II-179-86; discussion 186-7.
Matsushita, et al., *Circulation*, 100:262-268, 1999.
McConnell, et al., *J. Thorac. Cardiovasc. Surg.*, 130:1001 2005.
Menasche, et al., *C R Biologies*, 325:731-738, 2002.
Menasche, et al., *Heart Failure Reviews*, 8:221-227, 2003.
Menasche, et al., *J. Am. Coll. Cardiol.*, 41:1078-1083, 2003.
Menasche, et al., *Lancet*, 357:279-280, 2001.
Migrino, et al., *Circulation*, 96:116-121, 1997.
Minami, et al., *J. Am. Coll. Cardiol.*, 41:1084-1086, 2003.
Mitchell, et al., *J. Am. Coll. Cardiol.*, 19:1136-1144, 1992.
*Morbidity & Mortality Weekly Report*, 50:90-93, 2001.
Murry, et al., *J. Clin. Invest.*, 98:2512-2523, 1996.
O'Connell, et al., *J. Heart Lung Transplant*, 13:S107-S112, 1994.
Oh, et al., *Proc. Natl. Acad. Sci. U.S.A.*, 100:12312-12318, 2003.
Orlic, et al., *Ann. N. Y. Acad. Sci.*, 938:221-230, 2001.
Orlic, et al., *Nature*, 410:701-704, 2001.
Orlic, et al., *Proc. Natl. Acad. Sci. U.S.A.*, 98:10344-10349, 2001.
Oron, et al., *Int. J Cardiovasc. Intervent.*, 3:227-230, 2000.
Pagani, et al., *J. Am. Coll. Cardiol.*, 41:879-888, 2003.
Perin, et al., *Circulation*, 107:2294-2302, 2003.
Pfeffer, et al., *Annu. Rev. Med.*, 46:455-466, 1995.
Pfeffer, et al., *Circulation*, 81:1161-1172, 1990.
Pouzet, et al., *Ann. Thorac. Surg.*, 71:844-851, 2001.
Recchia, et al., *Cir. Res.*, 83:969-979, 1998.
Reinecke, et al., *Circulation*, 100:193-202, 1999.
Reinecke, et al., *J. Mol. Cell. Card.*, 34:251-253, 2002.
Retuerto, et al., *J. Thorac. Cardiovasc. Surg.*, 127:1-11, 2004.
Rose, et al., *NEJM*, 345:1435-1443, 2001.
Sabbah, et al., *Am. J. Physiol.*, 260:H1379-1384, 1991.
Sakai, et al., *J. Thorac. Cardiovasc. Surg.*, 118:715-725, 1999.
Schroeder, et al., *Current Medical Diagnosis & Treatment*(Appleton & Langee, Connecticut), 257-356, 1992.
Scorsin, et al., *J. Thorac. Cardiovasc. Surg.*, 119:1169-1175, 2000.
Skulstad, et al., *Circulation*, 106:718-724, 2002.
Suga, et al., *Physiol. Rev.*, 70:247-277, 1990.
Suzuki, et al., *Circulation*, 102:359-364, 2000.
Takaoka, et al., *Cardiovasc. Res.*, 28:1251-1257, 1994.
Tambara, et al., *Circulation*, 108:259-263, 2003.
Taylor, et al., *J. Heart Lung Transplant*, 22:616-624, 2003.
Taylor, et al., *Nat. Med.*, 4:929-933, 1998.
Taylor, et al., *Proc. Assoc. Am. Physicians*, 109:245-253, 1997.
Terada, et al., *Nature*, 416:542-545, 2002.
Todaka, et al., *Am. J. Physiol.*, 272:H186-194, 1997.
Toma, et al., *Circulation*, 105:93-98, 2002.
Tomita, et al., *Circulation*, 100:247-256, 1999.
Torrent-Guasp, et al., *Semin. Thor. and Cardiovasc. Surg.*, 13:298-416, 2001.
Tse, et al., *Lancet*, 361:47-49, 2003.
Wang, et al., *J Thorac. Cardiovasc. Surg.*, 120:999-1006, 2000.
White, et al., *Circulation*, 76:44-51, 1987.
Ying, et al., *Nature*, 416:545-548, 2002.
Yoo, et al., *Circulation*, 102:204-209, 2000.
Zhang, et al., *Circulation*, 108:623, 2003.
Zhang, et al., *J. Mol. Cell. Cardiol.*, 33:907-921, 2001.
Taylor, Doris A., Cell-based myocardial repair: How should we proceed?, International Journal of Cardiology, 95 Suppl. 1 (2004) S8-S12.
Allanore, et aL, "Effects of Corticosteroids and Immunosuppressors on Idiopathic Inflammatory Myopathies-related Myocarditis evaluated by Magnetic Resonance Imaging," *Annals of the Rheumatic Diseases*, 64: 74-75, 2005.
Allen, et aL, *J. Cell Physiology*, 149:525-535, 1991.
Ansari, et al., *J. Allergy Clin. Immunol.*, 80:229-235, 1987.
Atkins, et al., *Ann. Thorac. Surg.*, 67(1):124-129, 1999.
Atkins et al., *J. Heart Lung Transplant*, 18(2):1173-1180, 1999.
Benabdallah, et al., "Improved Success of Myoblast Transplantation in *mdx*Mice by Blocking the Myostatin Signal," *Transplantation*, 79: 1696-1702, 2005.
Bouchentouf, et al., "Real-time Imaging of Myoblast Transplantation Using the Human Sodium Iodide Symporter," *BioTechn.*, 38: 937-942, 2005.
Brasselet, et al., "Skeletal Myoblast Transplantation Through a Catheter-Based Coronary Sinus Approach: An Effective Means of Improving Function of Infarcted Myocardium," *Europ. Heart Journal*, 26; 1551-1556, 2005.
Bujold, et al., "Autotransplantation in Mdx Mice of Mdx Myoblasts Genetically Corrected by an HSV-1 Amplicon Vector," *Cell Transplant*, 11: 759-767, 2002.
Camirand, et al., "Novel Duchenne Muscular Dystrophy Treatment Through Myoblast Transplantation Tolerance With Anti-CD45RB, Anti-CD154 and Mixed Chimerism," *Am J. Transplant*, 4: 1255-1265, 2004.
Campeau, et al., "Transfection of Large Plasmids in Primary Human Myoblasts," *Gene Ther.*, 8:1387-1394, 2001.
Chiu, et al., *Ann. Thorac . . . Surg.*, 60(1):12-18, 1995.
Coirault, et al., *Circulation*, 114(18, Suppl. S):198, 2006.
Desnuelle, et al., "The Possible Place of Autologus Cell Therapy in Facioscapulohumeral Muscular Dystrophy," *Bull Acad. Natl. Med.*, 189: 697-714, 2005. (Abstract only).
Drouin, et al., "Adult Muscle-derived Stem Cells Culture," *Abstracts of Papers Am. Chem. Soc.*, 229: U200, 2005.
Duboc, et al., "Effect of Perindopril on the Onset and Progression of Left Ventricular Dysfunction in Duchenne Muscular Dystrophy," *J. Am. Coll. Cardiol.*, 45: 855-857, 2005.
El Fahime, et al., "In Vivo Migration of Transplanted Myoblasts Requires Matrix Metalloproteinase Activity," *Exp. Cell. Res.*, 258: 279-287, 2000.
Foster, et al., *J. of Cell Biology*, 105(4 part 2):288A, 1987.
Fromes, et a., "Gene Delivery to the Myocardium by Intrapericardial Injection," *Gene Ther.*, 6: 683-688, 1999.
Gold, et al., *Abstracts from the 70th Scientific Sessions*, 3170:1-567, 2010.
Grepin, et al., *Development*, 124(12):2387-2895, 1997.
Guerette, et al., "Efficient Myoblast Transplantation in Mice Immunosuppressed With Monoclonal Antibodies and CTLA4 Ig," *Transplant Proc.*, 29: 1932-1934, 1997.

(56) References Cited

OTHER PUBLICATIONS

Guerette, et al., "Immunosuppression With Monoclonal Antibodies and CTLA4-Ig After Myoblast Transplantation in Mice," *Transplantation*, 62: 962-967, 1996.
Gussoni, et al., *Nature*, 356:435-438, 1992.
Hagege, A.A, et al., "Viability and Differentiation of Autologous Skeletal Myoblast Grafts in Ischaemic Cardiomyopathy.", *The Lancet*361: 491-492, 2003.
Hagege, et al., "Skeletal myoblast transplantation in ischemic heart failure: long-term follow-up of the first phast I cohort of patients", *Circulation*, 114(Suppl. 1): 1108-13, Jul. 4, 2006.
Hagege, et al., *Hypertension*, 38(6):1413-1415, 2001.
Kao, et al., "Satellite Cells for Myocardial Regenerating", Abstract, *Cardiac Muscle Physiology*, 32: 220, 1989.
Kao, et al., *Circulation Supp. II*, 84(4):1I-386, 1995.
Klug, et al., *J. Clin. Invest.*, 98(1):216-224, 1996.
Koh, et al., *J. Clin. Invest.*, 92(3):1548-1554, 1993.
Koh, et al., *J. Clin. Invest.*, 95(1):114-121, 1995.
Lafreniere, et al., "Growth factors improve the in vivo migration of human skeletal myoblasts by modulating their endogenous proteolytic activity", *Transplantation*, 77(11): 1741-7, Jun. 15, 2004.
Lafreniere, et al., "Interleukin-4 improves the migration of human myogenic precursor cells in vitro and in vivo", *Experimental Cell Research*, 312(7): 1127-41, Apr. 15, 2006.
Leobon, et al., "Evidence for In Vivo Coupling Between Transplanted Embryonic Stem Cells and Host Cardiomyocytes," *Circulation*, 112: U146, 2005.
Leor, et al., Transplantation of Fetal Myocardial Tissue into the Infarcted Myocardium of Rat, a Potential Method for Repair of Infarcted Myocardium? *Circulation*, 94:(Supplement II), II-332-II336, 1996.
Leor, et al., *Cardiovasc. Res.*, 35(3):431-441, 1997.
Li, et al., *Ann. Thorac. Surg.*, 62(3):654-661, 1996.
Li, et aL, *Can. J. Cardiol.*, 14(5):735-744, 1998.
Li, et al., *Cardiovasc. Res.*, 32(2):362-373, 1996.
Li, et al., *Cir. Res.*, 78(2):283-288, 1996.
Li, et al., *Circulation*, 96(9 Suppl):II-179-187, 1997.
Li, et al., *J. Mol. Cell. Cardiol.*, 26:A162, 1994.
Li, et al., *J. Tiss. Cult. Meth.*, 14:93-100, 1992.
Macgovern, et al., *Ann. Thorac. Surg.*, 61(1):413-419, 1996.
Mannion, et al., *Circ. Res.*, 58(2):298-304, 1986.
Maurel, et al., "Can Cold or Heat Shock Improve Skeletal Myoblast Engraftment in Infarcted Myocardium?" *Transplantation*, 80: 660-665, 2005.
Maurel, et al., "Patterns of Cell Death and Proliferation After Skeletal Myoblast Transplantation," *Europ. Heart Journal*, 25: 265, 2004.
Menasche, "Cardiac Myoblasts," *Ernst Schering Res. Foundation Workshop*, 21-34, 2005.
Menasche, "Role of Stem Cells in Cardiac Repair," *Bull Acad. Natl. Med.*, 189: 615-624, 2005. (Abstract only).
Menasche, "Stem Cells for Clinical Use in Cardiovascular Medicine—Current Limitations and Future Perspectives," *Thrombosis and Haemostasis*, 94: 697-701, 2005.
Menasche, et al., "Autologous skeletal myoblast transplantation for severe postinfarction left ventricular dysfunction", *J. Am Coll Cardiol*, 41(7): 1078-83, Apr. 2, 2003.
Menasche, et al., "Cell Transplantation in Myocardium", *Ann Thorac Surg*, 75: S20-S28, 2003.
Menasche, et al., *Arch. Mal. Coeur. Vaiss.*, 94(3):180-182, 2001.
Menasche, et al., *Circulation*, 114(22):2426, 2006.
Menasche, *Progress in Cardiovascular Diseases*, 50(1):7-17, 2007.
Messas, et al., "Autologous myoblast transplantation for chronic ischemic mitral regurgitation", *J. Am Coll Cardiol*, 47(10): 2086-93, May 16, 2006.
Messas, et al., "Chordal cutting does not adversely affect left ventricle contractile function", *Circulation*, 114(1Suppl): 1521-8, Jul. 4, 2006.

Meune and Duboc, "Can Perindopril Delay the Onset of Heart Failure in Duchenne Muscular Dystrophy?" *J. of Am. College of Cardiology*, 46: 1782, 2005.
Meune, et al., "Cardiac Involvement in Female Carriers of Duchenne and Becker Muscular Dystrophy," *Circulation*, 110: 362, 2004.
Mills, et al., *Exp. Cell. Res.*, 313(3):527-537, 2007.
Moisset, et al., "Expression of Human Dystrophin Following the Transplantation of Genetically Modified mdx Myoblasts," *Gene Ther.*, 5: 1340-1346, 1998.
Moisset, et al., "Successful Transplantation of Genetically Corrected DMD Myoblasts Following Ex Vivo Transduction With the Dystrophin Minigene," *Biochem Biophys Res. Commun.*, 247: 94-99, 1998.
Morrow, et al., *J. Clin. Invest.*, 85(6):1816-1820, 1990.
Muchir, et aL, "Nuclear Envelope Alterations in Fibroblasts From Patients With Muscular Dystrophy, Cardiomyopathy, and Partial Lipodystrophy Carrying Lamin A/C Gene Mutations," *Muscle & Nerve*, 30: 444-450, 2004.
Murry, et al., "Cell-Based Cardiac Repair," *Circulation*, 112: 3174-3183, 2005.
Murry, et al., *Circulation*, Suppl. 1:92(8):1995.
Murry, et al., *J. Clin. Invest.*, 98(11):2512-2523, 1996.
Neumeyer, et al., *Neurology*, 42(12):2258-2262, 1992.
Peault, et al., *Mol. Ther.*, 15(5):867-877, 2007.
Pitard, et al., "A Nonionic Amphiphile Agent Promotes Gene Delivery In Vivo to Skeletal and Cardiac Muscles," Hum. Gene Ther., 13: 1767-1775, 2002.
Pouzet, et al., *J. Soc. Biol.*, 195(1):47-49, 2001.
Quenneville, et al., "Nucleofection of Muscle-Derived Stem Cells and Myoblasts With phiC31 Integrase: Stable Expression of a Full-length-dystrophin Fusion Gene by Human Myoblasts," *Mol. Ther.*, 10: 679-687, 2004.
Retuerto, et al., *J. Thorac . . . Cardiovasc. Surg.*, 133(2):478-484, 2007.
Robinson, et al., *Cell Transplant*, 5(1):77-91, 1996.
Schwartz and Mercadier, "Molecular and Cellular Biology of Heart Failure," *Curr. Opin. Cardiol.*, 11: 227-236, 1996.
Schweitzer, et al., *Exp. Cell Res.*, 172(1):1-20, 1987.
Siepe, et al., *Artificial Organs*, 31(6):425-433, 2007.
Skuk, et al., "Dystrophin Expression in Muscles of Duchenne Muscular Dystrophy Patients After High-density Injections of Normal Myogenic Cells," *J. Neuropathol Exp. Neurol.*, 65: 371-386, 2006.
Skuk, et al., "Experimental and Therapeutic Approaches to Muscular Dystrophies," *Curr. Opin. Neurol.*, 15: 563-569, 2002.
Skuk, et al., *Transplantation*, 84(10):1307-1315, 2007.
Soonpaa, et al., *Ann. N.Y. Acad. Sci.*, 752:446-454, 1995.
Soonpaa, et al., *Science*, 264:98-101, 1994.
Stephan, et al., *Cell Transplantation*, 16(4):391-402, 2007.
Suzuki, et al., *Circulation*, 104(12Suppl):I207-I212, 2001.
Suzuki, et al., *Circulation*, 104(12Suppl):I213-I217, 2001.
Taylor, et al., *Nat. Med.*, 4(8):929-933, 1998.
Taylor, et al., *Proc. Assoc. Am. Physicians*, 109(3):245-253, 1997.
Thompson, et al., *Science*, 257:868-870, 1992.
Torrente, et al., "Identification of a Putative Pathway for the Muscle Homing of Stem Cells in a Muscular Dystrophy Model," *J. Cell Biol.*, 162: 511-520, 2003.
Van Meter, et al., *J. Thorac. Cardiovasc. Surg.*, 110(5):1442-1448, 1995.
Vilquin, "Myoblast Transplantation: Clinical Trials and Perspectives," *Acta Myol.*, 24; 119-127, 2005.
Vilquin, et al., "Normal Growth and Regenerating Ability of Myoblasts From Unaffected Muscles of Facioscapulohumeral Muscular Dystrophy Patients," *Gene Therapy*, 12: 1651-1662, 2005.
Vilquin, et al., *Med. Sci.* (Paris), 20(6-7):651-652, 2004.
Wang, et al., *Blood*, 90(3):1075-1082, 1997.
Watanabe, et al., *Cell Transplant*, 7(3):239-246, 1998.
Yoon, et al., *Tex. Heart Inst. J.*, 22(2):119-125, 1995.

\* cited by examiner

CELLULAR CARDIOMYOPLASTY AS SUPPORTIVE THERAPY IN PATIENTS WITH HEART DISEASE

RELATED APPLICATIONS

The present application claims priority under 35 U.S.C. §119(e) to U.S. provisional patent application, U.S. Ser. No. 60/678,976, filed May 9, 2005, which is incorporated herein by reference.

BACKGROUND OF THE INVENTION

Despite dramatic advances in the treatment of heart disease over the past three decades, coronary artery disease (CAD) remains the leading cause of death in the Western world ("Mortality from coronary heart disease and acute myocardial infarction" *Morbidity & Mortality Weekly Report* 50:90-93, 2001; incorporated herein by reference). More specifically, while preventative measures and "mechanical" revascularization strategies (angioplasty and bypass surgery) have resulted in five year survival rates in excess of 80% for individuals who are candidates for such therapies, treatment options remain limited when coronary disease has progressed to diffuse, occlusive disease, and/or infarction (American Heart Association, Heart and Stroke Statistical Update, 2003; incorporated herein by reference). The two-year survival rate for individuals with such advanced coronary artery disease is as low as 20% (Anyanwu et al. "Prognosis after heart transplantation: transplants alone cannot be the solution for end stage heart failure" *BMJ* 326:509-510, 2003; incorporated herein by reference).

Each year, almost 1.1 million Americans suffer an acute myocardial infarction (American Heart Association, Heart and Stroke Statistical Update, 2003; incorporated herein by reference). Early intervention can limit infarct size and improve early survival (Mitchell et al. "Left ventricular remodeling in the year after first anterior myocardial infarction: a quantitative analysis of contractile segment lengths and ventricular shape" *J. Am. Coll. Cardiol.* 19:1136-44, 1992; Migrino et al. "End-systolic volume index at 90 and 180 minutes into reperfusion therapy for acute myocardial infarction is a strong predictor of early and late mortality" *Circulation* 96:116-121, 1997; Boyle et al. "Limitation of infarct expansion and ventricular remodeling by late reperfusion. Study of time course and mechanism in a rat model" *Circulation* 88:2872-83, 1993; each of which is incorporated herein by reference). However, 20% of those patients surviving an acute myocardial infarction will develop significant left ventricular dilatation with a left ventricular end-systolic volume index (LVESVI) of less than 60 mL/m$^2$. The GUSTO I trial (Migrino et al. "End-systolic volume index at 90 and 180 minutes into reperfusion therapy for acute myocardial infarction is a strong predictor of early and late mortality" *Circulation* 96:116-121, 1997; incorporated herein by reference) documented that left ventricular dilatation following myocardial infarction is an independent and significant predictor of mortality. Therefore, whereas early survival after myocardial infarction may be predicated by the timeliness and adequacy of appropriate reperfusion therapy, long-term prognosis is strongly dependent on subsequent changes in left ventricular geometry and function These are the determinants of congestive heart failure (Mitchell et al. "Left ventricular remodeling in the year after first anterior myocardial infarction: a quantitative analysis of contractile segment lengths and ventricular shape" *J. Am. Coll. Cardiol.* 19:1136-44, 1992; Gheorghiade et al. "Chronic heart failure in the United States, a manifestation of coronary artery disease" *Circulation.* 97:282-89, 1998; White et al. "Left ventricular end-systolic volume as the major determinant of survival after recovery from myocardial infarction" *Circulation* 76(1):44-51, 1987; each of which is incorporated herein by reference).

Congestive heart failure (CHF), which can result from an acute myocardial infarction, currently affects over 5 million people in the United States (National Heart Lung and Blood Institute National Institutes of Health Data Fact Sheet: congestive heart failure in the United States: A new epidemic. NHLBI web site. www/nhlbi.nih.gov/health/public/heart/other/chf.htm; O'Connell et al. "Economic impact of heart failure in the United States: time for a different approach" *J. Heart Lung Transplant.* 13:S107-S112, 1994; each of which is incorporated herein by reference). Medical therapies, despite some progress, still confer only a <50% one-year survival in patients with the most severe clinical manifestations of end-stage CHF (Rose et al. "Long-term use of a left ventricular assist device for end-stage heart failure" *NEJM* 345(20):1435-43, 2001; incorporated herein by reference). Despite its clinical effectiveness, heart transplantation is a therapy with little epidemiological significance in the fight against heart failure (Taylor et al. "The registry of the international society of heart and lung transplantation: 20$^{th}$ official adult heart transplant report-2003" *J. Heart Lung Transplant.* 22(6):616-624, 2003; incorporated herein by reference). As a result, cell-based therapies for repair and regeneration of infarcted myocardium have been proposed to treat patients suffering from chronic heart failure (Chiu et al. "Cellular cardiomyoplasty: myocardial regeneration with satellite cell implantation" *Ann. Thor. Surg.* 60:12-8, 1995; Pagani et al. "Autologous skeletal myoblasts transplanted to ischemia-damaged myocardium in humans" *J. Am. Coll. Cardiol.* 41:879-888, 2003; Ghostine et al. "Long-term efficacy of myoblast transplantation on regional structure and function after myocardial infarction" *Circulation* 106[suppl I]:I131-6, 2002; Dorfmaan et al. "Myocardial tissue engineering with autologous myoblast implantation" *J. Thor. Cardiovasc. Surg.* 116:744-51, 1988; Taylor et al. "Regenerating functional myocardium: improved performance after skeletal myoblast transplantation" *Nat. Med* 4(8):929-33, 1998; Retuerto et al. "Angiogenic pre-treatment improves the efficacy of cellular cardiomyoplasty performed with fetal cardiomyocyte implantation" *J. Thorac. Cardiovasc. Surg.* 127:1-11, 2004; Jain et al. "Cell therapy attenuates deleterious ventricular remodeling and improves cardiac performance after myocardial infarction" *Circulation* 103:1920-27, 2001; Reinecke et al. "Evidence for fusion between cardiac and skeletal muscle cells" *Circ. Res.* 94(6):e56-60, 2004; McConnell et al. "Correlation of autologous skeletal myoblast survival with changes in left ventricular remodeling in dilated ischemic heart failure" *J. Thorac. Cardiovasc. Surg.* 2004 (in press); Kessler et al. "Myoblast cell grafting into heart muscle: cellular biology and potential applications" *Annu. Rev. Physiol.* 61:219-42, 1999; Yoo et al. "Heart cell transplantation improves heart function in dilated cardiomyopathic hamsters" *Circulation.* 102(19 Suppl 3):III204-9, 2000; Koh et al. "Stable fetal cardiomyocyte grafts in the hearts of dystrophic mice and dogs" *J. Clin. Invest.* 96(4):2034-42, 1995; Klug et al. "Genetically selected cardiomyocytes from differentiating embronic stem cells form stable intracardiac grafts" *J. Clin. Invest.* 98(1):216-24, 1996; Jackson et al. "Regeneration of ischemic cardiac muscle and vascular endothelium by adult stem cells" *J. Clin. Invest.* 107(11): 1395-402, 2001; Kocher et al. "Neovascularization of ischemic myocardium by human bone marrow derived angioblasts prevents cardiomyocyte apoptosis, reduces remodeling and improves cardiac function" *Nature Medicine* 7:430-436, 2001; Kamihata et al. "Implantation of bone marrow mononuclear cells into ischemic myocardium enhances collateral perfusion and regional function via side supply of angioblasts, angiogenic ligands, and cytokines" *Circulation* 104:1046-1052, 2001; Orlic et al. "Transplanted adult bone marrow cells repair myocardial infarcts in mice" *Ann. N.Y. Acad. Sci.* 938:221-9, discussion 229-30, 2001; Orlic et al. "Mobilized bone marrow cells repair the infarcted heart, improving function and survival" *Proc. Natl. Acad. Sci. U.S.A.* (98): 10344-9, 2001; Balsam et al. "Haematopoietic stem cells adopt mature haematopoietic fates in ischaemic myocardium" *Nature* 428(6983):668-73, 2004; Reinecke et al. "Taking the toll after cardiomyocyte grafting: a reminder of the importance of quantitative biology" *J. Mol. Cell. Card.* 34:251-253, 2002; Perin et al. "Transendocardial, autologous bone marrow cell transplantation for severe, chronic ischemic heart failure" *Circulation* 107:2294-2302, 2003; Tse et al. "Angiogenesis in ischaemic myocardium by intramyocardial autologous bone marrow mononuclear cell implantation" *Lancet* 361:47-49, 2003; Kamihata et al. "Implantation of bone marrow mononuclear cells into ischemic myocardium enhances collateral perfusion and regional function via side supply of angioblasts, angiogenic ligands, and cytokines" *Circulation* 104: 1046-1052, 2001; each of which is incorporated herein by reference). Immature cells are grafted into the heart in key areas of myocardial dysfunction with the goal of angiogenesis, vasculogenesis, and/or myogenesis to promote functional and geometric restoration. Unfortunately, current results in human clinical trials demonstrate that cellular graft survival number is very poor with typically <1% of autologous myoblasts surviving implantation (Pagani et al. "Autologous skeletal myoblasts transplanted to ischemia-damaged myocardium in humans." *J. Am. Coll. Cardiol.* 41:879-888, 2003; incorporated herein by reference). The reason for such poor cell survival and engraftment is unknown.

Cell transfer is generally thought to provide for the regeneration of cardiac function in the setting of myocardial infarction by: (1) "repopulating" scarred myocardium with contractile myocytes; (2) providing a "scaffolding" to diminish further remodeling of the thinned, injured ventricle; and/or (3) serving as a vehicle for the angiogenic stimulation of ischemic myocardium (Scorsin et al. "Comparison of the effects of fetal cardiomyocyte and skeletal myoblast transplantation on postinfarction left ventricular function" *J. Thorac. Cardiovasc. Surg.* 119:1169-75, 2000; Jain et al. "Cell therapy attenuates deleterious ventricular remodeling and improves cardiac performance after myocardial infarction" *Circulation* 103:1920-1927, 2001; Suzuki et al. "Development of a novel method for cell transplantation through the coronary artery" *Circulation* 102[suppl III]:III-359-111-364, 2000; Orlic et al. "Bone marrow cells regenerate infarcted myocardium" *Nature* 410:701-704, 2001; Wang et al. "Marrow stromal cells for cellular cardiomyoplasty: feasibility and potential" *J. Thorac. Cardiovasc. Surg.* 120:999-1006, 2000; Tomita et al. "Autologous transplantation of bone marrow cells improves damaged heart heart function" *Circulation* 100[suppl II]:II-247-II-256, 1999; Reinecke et al. "Survival, Integration, and differentiation of cardiomyocyte grafts: a study in normal and injured rat hearts" *Circulation* 100:193-202, 1999; Sakai et al. "Cardiothoracic transplantation. Fetal cell transplantation: a comparison of three cell types" *J. Thorac. Cardiovasc. Surg.* 118:715-25, 1999; Chedrawy et al. "Incorporation and integration of implanted myogenic and stem cells into native myuocardial fibers: anatomic basis for functional improvements" *J. Thorac. Cardiovasc. Surg.* 124: 584-90, 2002; Klug et al. "Genetically selected cardiomyocytes from differentiating embryonic stem cells form stable intracardiac grafts" *J. Clin. Invest.* 98:216-224, 1996; Atkins et al. "Intracardiac transplantation of skeletal myoblasts yields two populations of striated cells in situ" *Ann. Thorac. Surg.* 67:124-9, 1999; Leor et al. "Transplantation of fetal myocardial tissue into the infarcted myocardium of rat. A potential method for repair of infarcted myocardium?" *Circulation* 94 [suppl II]:II-332-II-336, 1996; Zhang et al. "Cardiomyocyte grafting for cardiac repair: graft cell death and anti-death strategies" *J. Mol. Cell. Cardiol.* 33:907-921, 2001; Li et al. "Natural history of fetal rat cardiomyocytes transplanted into adult rat myocardial scar tissue" *Circulation* 96[suppl II]:II-179-II-187, 1997; Taylor et al. "Regenerating functional myocardium: improved performance after skeletal myoblast transplantation" *Nature Medicine* 4:929-933, 1998; Menasché, "Cell therapy of heart failure" *C R Biologies* 325: 731-738, 2002, Oh et al. "Cardiac progenitors from adult myocardium: homing, differentiation and fusion after infarction" *Proc. Natl. Acad. Sci. USA* 100:12313-18, 2003; Terada et al. "Bone marrow cells adopt the phenotype of other cells by spontaneous cell fusion" *Nature* 416:542-5, 2002; Ying et al. "Changing potency by spontaneous fusion" *Nature* 416: 545-8, Apr. 4, 2002; each of which is incorporated herein by reference). It is unknown which if any of these mechanisms is relevant to the putative efficacy of cellular cardiomyoplasty (CCM). In this regard, the typically extremely inefficient (<10%) observed engraftment of cells into areas of myocardial scar has been cited as a potential explanation for the relatively limited improvements in ventricular function noted after cell implantation in animal studies (Pagani et al. "Autologous skeletal myoblasts transplanted to ischemia-damaged myocardium in humans: Histological analysis of cell survival and differentiation" *J. Am. Coll. Cardiol.* 41:879-88, 2003; Matsushita et al. "Formation of cell junctions between grafted and host cardiomyocytes at the border zone of rat myocardial infarction" *Circulation* 100[suppl II]: II-262-II-268, 1999; Kehat et al. "Human embryonic stem cells can differentiate into myocytes with structural and functional properties of cardiomyocytes" *J. Clin. Invest.* 108:407-414, 2001; Boheler et al. "Differentiation of pluripotent embryonic stem cells into cardiomyocytes" *Circ. Res.* 91:189-201, 2002; Toma et al. "Human mesenchymal stem cells differentiate to a cardiomyocyte phenotype in the adult murine heart" *Circulation* 105:93-98, 2002; Tambara et al. "Transplanted skeletal myoblasts can fully replace the infracted myocardium when they survive in the host in large numbers" *Circulation* 108[suppl II]:II-259-II-263, 2003; Minami et al. "Skeletal muscle meets cardiac muscle" *J. Am. Coll. Cardiol.* 41:1084-6, 2003; Ghostine et al. "Long-term efficacy of myoblast transplantation on regional structure and function after myocardial infarction" *Circulation* 100[suppl I]:I-131-I-136, 2002; each of which is incorporated herein by reference), and has raised doubts as to the importance of the persistent physical presence of cell implants in myocardial scar, as opposed to their potential role as a transient mediator of angiogenesis (Scorsin et al. "Comparison of the effects of fetal cardiomyocyte and skeletal myoblast transplantation on postinfarction left ventricular function" *J. Thorac. Cardiovasc. Surg.* 119:1169-75, 2000; Reinecke et al. "Survival, Integration, and differentiation of cardiomyocyte grafts: a study in normal and injured rat hearts" *Circulation* 100:193-202, 1999; Zhang et al. "Cardiomyocyte grafting for cardiac repair: graft cell death and anti-death strategies" *J. Mol. Cell. Cardiol.* 33:907-921, 2001; Menasche, "Cell therapy of heart failure" *C. R. Biologies* 325:731-738, 2002; each of which is incorporated herein by reference). Also, while the efficacy of CCM has been idealized to involve the differentiation of stem cells into functional cardiomyocytes, evidence of such differentiation may have been confounded by the potential occurrence of cell fusion between implanted stem cells and host myocytes (Oh et. al. "Cardiac progenitors from adult myocardium: homing, differentiation and fusion after infarction" *Proc. Natl. Acad. Sci. USA* 100:12313-18, 2003; Terada et al. "Bone marrow cells adopt the phenotype of other cells by spontaneous cell fusion" *Nature* 416:542-5, 2002; Ying et al. "Changing potency by spontaneous fusion" *Nature* 416:545-48, Apr. 4, 2002; each of which is incorporated herein by reference). Skeletal myoblast transplantation though has been demonstrated to provide functional advantages over fibroblast implants in cardiomyoplasty studies (Scorsin et al. "Comparison of the effects of fetal cardiomyocyte and skeletal myoblast transplantation on postinfarction left ventricular function" *J. Thorac. Cardiovasc. Surg.* 119:1169-75, 2000; Jain et al. "Cell therapy attenuates deleterious ventricular remodeling and improves cardiac performance after myocardial infarction" *Circulation* 103:1920-1927, 2001; Sakai et al. "Cardiothoracic transplantation. Fetal cell transplantation: a comparison of three cell types" *J. Thorac. Cardiovasc. Surg.* 118:715-25, 1999; Taylor et al. "Regenerating functional myocardium: improved performance after skeletal myoblast transplantation" *Nature Medicine* 4:929-933, 1998; each of which is incorporated herein by reference).

Given the use of cellular cardiomyoplasty to treat heart disease and the progress being made in this field, there remains a need for treatments of damage to heart tissue using cellular cardiomyoplasty. Also, given the recent advent of this treatment, the issue remains of how this treatment method can best be used in the treatment of patients suffering with various types and severity of heart disease.

SUMMARY OF THE INVENTION

The present invention stems from the recognition that cell transplantation may help allow damaged hearts to recover so that cardiac transplantation or other further therapy can be delayed or avoided. In certain embodiments, the present invention involves the selection of patients with heart disease as candidates for cellular cardiomyopathy and/or determines how cellular cardiomyopathy should be used in the management of the selected patient's disease. The present invention provides for using cellular cardiomyoplasty in the treatment of patients suffering from a wide variety of heart diseases, including those with different etiologies, severities, prognoses, etc. (e.g., ischemic heart disease, congestive heart failure, acute versus chronic heart disease, cardiogenic shock). The present invention includes the recognition that cellular cardiomyoplasty may be a "destination therapy" or "bridge to recovery" for some patients.

In one aspect, cellular cardiomyoplasty may be used as a "bridge to recovery." To improve cardiac function, the patient's heart is implated with cells such as skeletal myoblasts. Cellular cardiomyoplasty may be used alone or in conjunction with other treatment modalities such as left ventricular assist devices, cardiac surgery, transplantation, or medications. In certain embodiments, the cellular cardiomyoplasty may eliminate the need for such invasive procedures as heart surgery or orthotopic cardiac transplantation. The cellular cardiomyoplasty improves cardiac function, for example, reversing, preventing, or reducing the remodeling of the heart. In certain embodiments, the cellular cardiomyoplasty prevents LV dilatation and/or reduces LV size (e.g., maintain left ventricular end-systolic index (LVESI) above 60 mL/m$^2$) to allow the patient to survive until cardiac transplantation. In certain embodiments, the cellular cardiomyopathy provides an improvement in cardiac function such that the patient does not need hospitalization, hospitalization stay is reduced, or the need for re-hospitalization is reduced. In certain embodiments, the cellular cardiomyopathy offers improved quality of life as compared to those patients who do not receive cellular cardiomyopathy. In certain embodiments, mortality rates are reduced for patients treated with cellular cardiomyoplasty.

The present invention also provides methods of selecting patients who are candidates for cellular cardiomyoplasty based on certain clinical criteria. The method also provides a method of selecting patients for treatment with cellular cardiomyoplasty as a "bridge to recovery." The criteria used to determine whether a patient is a candidate for such treatment may include ejection fraction (e.g., left ventricular ejection fraction), left ventricular end-systolic volume index, left ventricular end-diastolic volume index, cardiac output, blood pressure, stress testing, echocardiography or other imaging of the heart, EKG, etc. In certain embodiments, the patient selected for cellular cardiomyoplasty suffers from diffuse ischemic heart disease. In certain other embodiments, the patient may suffer from cardiogenic shock, for example, after a myocardial infarcation. In certain embodiments, the patient suffers from or is at risk for post-cardiotomy shock. In other embodiments, the patient suffers from myocarditis. In yet other embodiments, the patient suffers from a cardiomyopathy. In certain embodiments, the patient has a failed or failing heart transplant. In other embodiments, the patient selected for cellular cardiomyoplasty is not a candidate for heart transplant. In yet other embodiments, the patient is not a candidate for heart surgery such as coronary artery bypass grafting. In certain embodiments, the selected patient suffers from minor heart disease and can be managed with cellular cardiomyoplasty and medication. In certain embodiments, the selected patient suffers from acute heart disease. In other embodiments, the selected patient suffers from chronic heart disease.

Once a patient is selected as a candidate for cellular cardiomyoplasty, cells may optionally be implanted into the heart of the patient. Any technique for performing cellular cardiomyoplasty may be used. In certain embodiments, the cellular cardiomyoplasty is combined with pro-angiogenesis therapy as described in U.S. patent application, U.S. Ser. No. 60/666,932, filed Mar. 31, 2005, entitled "Treatment for Heart Disease," which is incorporated herein by reference. Cells that may be used in the inventive method include skeletal myoblasts, mesenchymal stem cells, cardiomyocytes, fetal cardiomyocytes, embryonic stem cells, fibroblasts, embryonic stem cells, and adult bone marrow-derived stem cells. In certain embodiments, skeletal myoblasts are used. In certain other embodiments, mesenchymal stem cells are implanted into the heart of the patient. The cells used may have been altered by the hand of man. The cells may be delivered by any means including, for example, by direct epicardial injection or by catheter based endocardial delivery (as described in U.S. patent application, U.S. Ser. No. 60/658,887, filed Mar. 4, 2005, which is incorporated herein by reference). The cells may be delivered during a surgical procedure. Cells may be administered multiple times. For example, cells may be administered by epicardial injection at the time of LVAD placement or other invasive procedure and then at a later time using a catheter. In certain embodiments, a side port needle is used to implant the cells (as described in U.S. patent application, U.S. Ser. No. 10/635,212, filed Aug. 6, 2003, which is incorporated herein by reference).

The invention provides both methods of selecting and methods of treating patients who are candidates for cardiomyoplasty as a "bridge to recovery." Once the patient has been chosen for treatment any technique for delivering cells into the heart, particularly the damaged area of the heart, may be used to treat the patient's heart disease. The present invention also includes kits (e.g., diagnostic kits, treatment kits), reagents, software, cell compositions, medical devices, etc. which may be useful in selecting and treating patients as a "bridge to recovery."

DEFINITIONS

Figure 1:
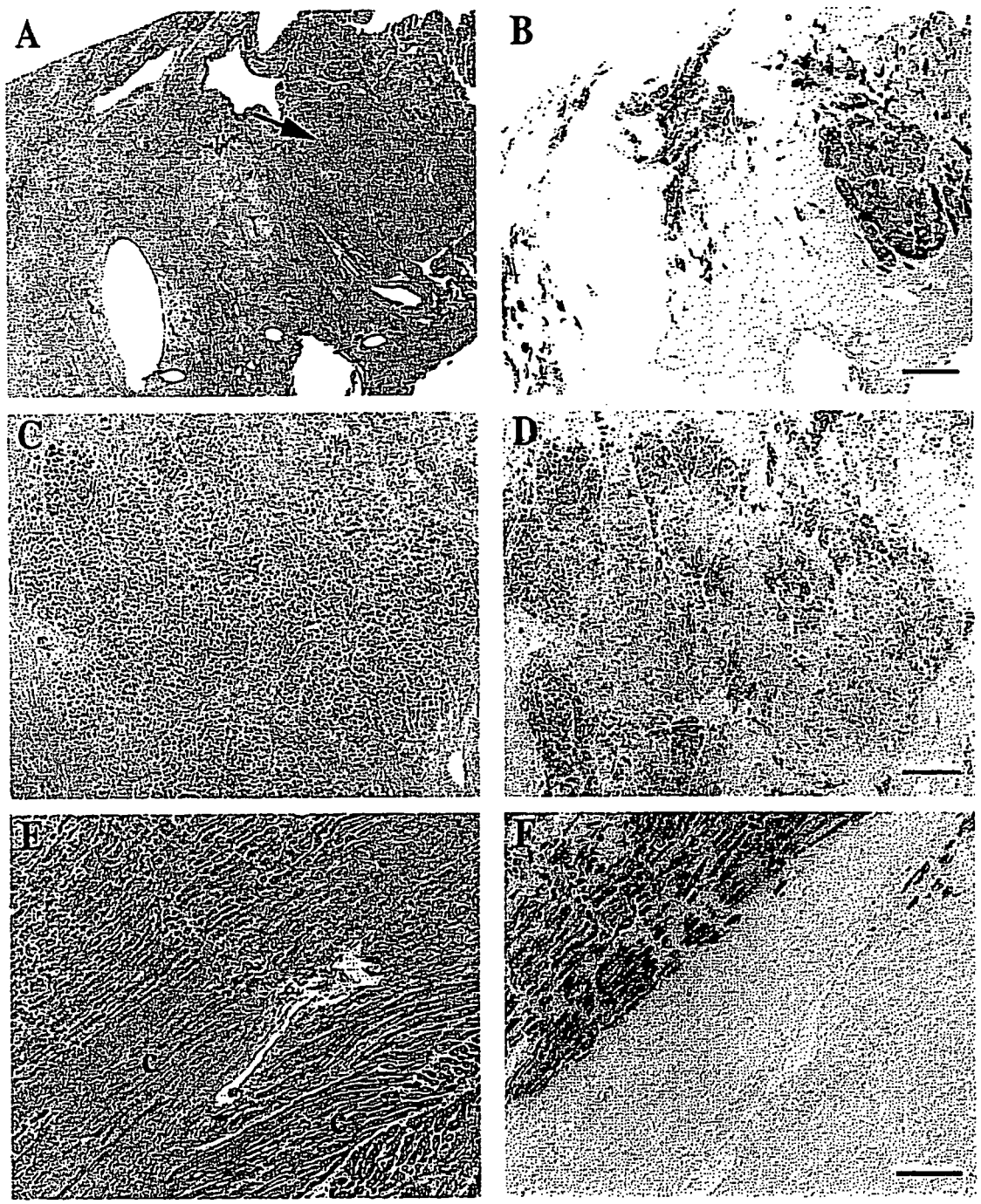
FIG. 1 shows stained sections six weeks after autologous skeletal myoblast (ASM) injection in sheep with ischemic heart failure (HF), composite Trichrome (A) and skeletal muscle specific myosin heavy chain (B, MY-32, purple staining) staining demonstrates extensive patches of ASM-derived skeletal muscle fibers engrafted in areas of myocardial scar. In panels C and D, at higher magnification from panel A (arrow), skeletal fibers were seen aligned with each other and further organized into myofibril bundles (Panels C and D). ASM-derived skeletal muscle aligned with remaining cardiac myocytes (Panel E, 'c') and with neighboring skeletal myofibers confirmed with staining for MY-32 (F). Scale bars in panels B, D and F are 2 mm, 0.5 mm, and 0.2 mm, respectively.

Angiogenesis refers to the formation of new blood vessels (e.g., capillaries). Particularly as used in the present invention, angiogenesis refers to the formation of new blood vessels in heart tissue into which cells are or will be implanted. In certain embodiments, cells are implanted into an ischemic zone, and angiogenesis is enhanced. Angiogenesis can occur, e.g. as a result of the act of transplanting the cells, as a result of ischemia, and/or as a result of administering a pro-angiogenic factor such as VEGF.

Cardiac damage or disorder characterized by insufficient cardiac function includes any impairment or absence of normal cardiac function or presence of an abnormal cardiac function, whether chronic or acute. Abnormal cardiac function can be the result of disease, injury, and/or aging. As used herein, abnormal cardiac function includes morphological and/or functional abnormality of a cardiomyocyte, a population of cardiomyocytes, cardiac tissue, myocardium, endocardium, epicardium, portion of the heart (e.g., left ventricle, right ventricle, left atrium, right atrium, septum, conduction system), or the heart itself. Non-limiting examples of morphological and functional abnormalities include physical deterioration and/or death of cardiomyocytes, abnormal growth patterns of cardiomyocytes, abnormalities in the physical connection between cardiomyocytes, under- or overproduction of a substance or substances by cardiomyocytes, failure of cardiomyocytes to produce a substance or substances which are produced by healthy cardiomyocytes, and transmission of electrical impulses in abnormal patterns or at abnormal times. Abnormalities at a more gross level include dyskinesis, reduced ejection fraction, changes as observed by echocardiography (e.g., dilatation), changes in EKG, changes in exercise tolerance, reduced capillary perfusion, and changes as observed by angiography. Abnormal cardiac function is seen with many disorders including, for example, ischemic heart disease, e.g., angina pectoris, myocardial infarction, chronic ischemic heart disease, hypertensive heart disease, pulmonary heart disease (cor pulmonale), valvular heart disease, e.g., rheumatic fever, mitral valve prolapse, calcification of mitral annulus, carcinoid heart disease, infective endocarditis, congenital heart disease, myocardial disease, e.g., myocarditis, dilated cardiomyopathy, hypertensive cardiomyopathy, cardiac disorders which result in congestive heart failure, and tumors of the heart, e.g., primary sarcomas and secondary tumors.

Derived from refers to a cell that is obtained from a sample or subject or is the progeny or descendant of a cell that was obtained from the sample or subject. A cell that is derived from a cell line is a member of that cell line or is the progeny or descendant of a cell that is a member of that cell line. A cell derived from an organ, tissue, individual, cell line, etc., may be modified in vitro after it is obtained. For example, the cell may be engineered to express a gene of interest. Such a cell is still considered to be derived from the original source.

Engrafts are the incorporation of transplanted muscle cells or muscle cell compositions into heart tissue with or without the direct attachment of the transplanted cell to a cell in the recipient heart (e.g., by the formation desmosomes or gap junctions). In certain embodiments, the cells enhance cardiac function, e.g., by increasing cardiac output, or prevent or slow decreases in cardiac function. In other embodiments, the engraft may provide a scaffold to prevent remodeling of the injured heart. In other embodiments, the engraft may stimulate angiogenesis. In certain embodiments, engraft may refer to the survival of transplanted cells in the heart.

Cell survival, myoblast survival, or fibroblast survival within the heart refers to any of the following and combinations thereof: (1) survival of the cells, myoblasts, or fibroblasts themselves; (2) survival of cells into which the cells, myoblasts, or fibroblasts differentiate; (3) survival of progeny of the cells, myoblasts, or fibroblasts; and (4) survival of fusion products (i.e., cells with which the cells, myoblasts, or fibroblasts fuse).

Myocardial ischemia refers to a lack of oxygen flow to the heart or portion thereof, resulting in myocardial ischemic damage. As used herein, the phrase myocardial ischemic damage includes damage caused by reduced blood flow to the myocardium. Non-limiting examples of causes of myocardial ischemia and myocardial ischemic damage include: decreased aortic diastolic pressure, increased intraventricular pressure and myocardial contraction, coronary artery stenosis (e.g., coronary ligation, fixed coronary stenosis, acute plaque change (e.g., rupture, hemorrhage), coronary artery thrombosis, vasoconstriction), aortic valve stenosis and regurgitation, and increased right atrial pressure. Non-limiting examples of adverse effects of myocardial ischemia and myocardial ischemic damage include myocyte damage (e.g., myocyte cell loss, myocyte hypertrophy, myocyte cellular hyperplasia), angina (e.g., stable angina, variant angina, unstable angina, sudden cardiac death), myocardial infarction, and congestive heart failure. Damage due to myocardial ischemia may be acute or chronic, and consequences may include scar formation, cardiac remodeling, cardiac hypertrophy, wall thinning, dilatation, and associated functional changes. The existence and etiology of acute or chronic myocardial damage and/or myocardial ischemia may be diagnosed using any of a variety of methods and techniques well known in the art including, e.g., non-invasive imaging (e.g., MRI, echocardiography), angiography, stress testing, assays for cardiac-specific proteins such as cardiac troponin, and evaluation of clinical symptoms. These methods and techniques as well as other appropriate techniques may be used to determine which subjects are suitable candidates for the treatment methods described herein.

A peptide or protein comprises a string of at least three amino acids linked together by peptide (amide) bonds. The term "peptide" may refer to an individual peptide or a collection of peptides. Inventive peptides often contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc.

Polynucleotide or oligonucleotide refers to a polymer of at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5 propynyl-cytidine, C5-bromouridine, C5-fluorouridine, C5-iodouridine, C5-propynyl-uridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

Small molecule refers to a non-peptidic, non-oligomeric organic compound. In certain embodiments, a small molecule is synthesized in the laboratory by total synthesis, partial synthesis, or semi-synthesis. In other embodiments, a small molecule is found in nature. Small molecules, as used herein, can refer to compounds that are "natural product-like", however, the term "small molecule" is not limited to "natural product-like" compounds. Rather, a small molecule is typically characterized in that it contains several carbon-carbon bonds, and has a molecular weight of less than 1500, although this characterization is not intended to be limiting for the purposes of the present invention.

Skeletal myoblasts and skeletal myoblast cells refer to precursors of myotubes and skeletal muscle fibers. The term skeletal myoblasts also includes satellite cells, mononucleate cells found in close contact with muscle fibers in skeletal muscle. Satellite cells lie near the basal lamina of skeletal muscle myofibers and can differentiate into myofibers. As discussed herein, some inventive compositions comprising skeletal myoblasts lack detectable myotubes and muscle fibers. The term cardiomyocyte includes a muscle cell which is derived from cardiac muscle. Such cells have one nucleus and, when present in the heart, are joined by intercalated disc structures.

Stem cell refers to any pluripotent cell that under the proper conditions will give rise to a more differentiated cell. The stem cell may be able to differentiate into multiple types of differentiated cells. Stem cells which may be used in accordance with the present invention include mesenchymal, muscle, cardiac muscle, skeletal muscle, fetal stem cells, and embryonic stem cells. Stem cells useful in the present invention may give rise to cardiac myocytes or other cells normally found in the heart. Stem cells can also be characterized by their ability (1) to be self-renewing and (2) to give rise to further differentiated cells. This has been referred to as the kinetic definition.

Treating as used herein refers to reducing or alleviating at least one adverse effect or symptom of myocardial damage or dysfunction. In particular, the term applies to treatment of a disorder characterized by myocardial ischemia, myocardial ischemic damage, cardiac damage, or insufficient cardiac function. Adverse effects or symptoms of cardiac disorders are numerous and well-characterized. Non-limiting examples of adverse effects or symptoms of cardiac disorders include: dyspnea, chest pain, palpitations, dizziness, syncope, edema, cyanosis, pallor, fatigue, and death. For additional examples of adverse effects or symptoms of a wide variety of cardiac disorders, see Robbins et al. (1984) *Pathological Basis of Disease* (W.B. Saunders Company, Philadelphia) 547-609; Schroeder et al., eds. (1992) *Current Medical Diagnosis & Treatment* (Appleton & Lange, Connecticut) 257-356.

DETAILED DESCRIPTION OF PREFERRED EMBODIMENTS

The present invention provides a system for selecting and optionally treating a patient suffering from heart disease using cellular cardiomyoplasty. In one embodiment, the invention provides a method of selecting and treating a patient suffering from heart diseases as a "bridge to recovery" or as a "destination therapy." In much the same way that ventricular assist devices have been thought of as bridges to transplantation or recovery (Kherani et al. "Ventricular Assist Devices as a Bridge to Transplant or Recovery" *Cardiology* 101:93-103, 2004; Hon et al. "Bridge to Recovery with the Use of Left Ventricular Assist Device and Clenbuterol" *Ann. Thorac. Surg.* 75:S36-41, 2003; each of which is incorporated herein by reference), the development of cellular cardiomyoplasty with its improved success in treating heart disease has led it to become a bridge to recovery in the management of heart disease. The treatment of patients suffering from heart disease using cellular cardiomyoplasty can reduce hospitalization, reduce the need for re-hospitalization, improve quality of life, and/or reduce mortality and morbidity.

The inventive system is useful in managing the care of any patient suffering from heart disease. Non-limiting examples of heart disease include cardiomyopathy, hypertrophic cardiomyopathy, dilated cardiomyopathy, atherosclerosis, coronary artery disease, ischemic heart disease, myocarditis, viral infection, parasitic infection, bacterial infection, wounds, hypertensive heart disease, valvular disease, congenital heart disease, myocardial infarction, congestive heart failure, arrhythmias, cardiogenic shock, post-cardiotomy shock, failed heart transplant, end-stage heart failure, etc. The inventive system is useful in selecting and treating patents suffering from diseases of the heart involving damage to cardiac tissue such as a loss of contractility (e.g., as might be demonstrated by a decreased ejection fraction). The inventive system is useful in selecting and treating patients suffering from diseases of the heart involving injury to the heart due to ischemia. The inventive system is useful in treating patients suffering from cardiogenic shock, myocarditis, or cardiomyopathy. The inventive system may also be used in treating a patient with a failed or failing heart transplant. The inventive system may also be used to treat a patient on a list for a heart transplant. The patient may suffer from chronic heart disease or acute heart disease. Any patient with heart disease may be considered using the inventive system for diagnosis and/or treatment with cellular cardiomyoplasty.

The inventive system is also not limited to the treatment of human but can be used in the treatment of any animal including domesticated animals or pets. The inventive system may also be used in experimental animals such as mice, rats, dogs, pigs, sheep, and primates (e.g., apes, chimpanzees, monkeys). The inventive system provides for the treatment of animals suffering from heart disease, particularly diseases involving the loss of contractility in the heart, ischemic heart disease, or diseases resulting in remodeling of the heart.

The patient is typically evaluated by a treating physician, nurse, physician's assistant, or other health care professional. The decision of whether to treat a patient with cellular cardiomyoplasty may be based on any number of criteria as would be appreciated by a treating physician. The criteria used by the health care professional may include age of the patient, condition of the patient, extent of disease, type of disease, prognosis, lifestyle of patient, physical examination, medical history, other diseases (e.g., diabetes, hypercholesterolemia, arrhythmias), clinical signs (e.g., blood pressure, heart rate, pulses, etc.), clinical symptoms (e.g., chest pain, breathlessness, dizziness, etc.), medical tests (e.g. cardiac enzymes, echocardiography or other imaging, EKG, stress test, angiography etc.), other diseases of the patient, cardiac parameters (e.g., ejection fraction, stroke volume, left ventricular end-systolic index (LVESI), cardiac output), echocardiography, Holter monitoring, MRI, PET, urinanalysis, etc. Example 1 details several citeria which may be used in selecting a patient for "bridge to recovery" treatment using cellular cardiomyoplasty. The treating clinician will evaluate these criteria and determine whether the patient is suitable for treatment using the inventive system. In certain embodiments, the patient's cardiac output is determined in deciding whether a patient is a candidate for cellular cardiomyoplasty as a bridge-to-recovery therapy.

In certain embodiments, the patient has ischemic heart disease. In certain embodiments, the patient suffers from diffuse coronary artery disease. In other embodiments, the patient has suffered a myocardial infarction. In yet other embodiments, the patient has undergone an invasive procedure such as angioplasty or coronary artery bypass grafting. The patient may be selected for treatment to prevent or reduce cardiac remodeling after a myocardial infarction or other ischemic disease. Without wishing to be bound by a particular theory, the cell transplantation may facilitate repair or replacement of dead or damaged myocardium. The patient may be selected for treatment to increase cardiac output.

In certain embodiments, cellular cardiomyoplasty is combined with other treatments. For example, cellular cardiomyoplasty may be combined with the use of drug therapy. In certain embodiments, cellular cardiomyoplasty is combined with administration of clenbuterol, a selective β-2 agonist. In other embodiments, cellular cardiomyoplasty is combined with cardiac transplantation. However, in certain embodiments, cellular cardiomyoplasty is combined with other treatments excluding cardiac transplant. The cellular cardiomyoplasty may be used in conjunction with the use of cardiac devices such as left ventricular assist devices, balloon pumps, or pacemakers. In certain embodiments, cellular cardiomyoplasty is combined with the use of a left ventricular assist device, optionally further combined with a medication such as clenbuterol. The use of the left ventricular assist device is continued until normal heart function has recovered enough to allow the patient to remain stable without recurrent chronic heart failure. Patients destined for recovery and removal of an LVAD with further support may benefit from cellular cardiomyoplasty resulting in improved quality of life, decreased morbidity, decreased mortality, reduced hospitalization stays, and/or reduce need for re-hospitalization.

In certain embodiments, even patients who do not recover sufficiently to warrant weaning from LVAD support could benefit from cellular cardiomyoplasty. Even without removing the LVAD, patients treated with cellular cardiomyoplasty could see improvements in cardiac function and quality of life with reduction in hospital stays, re-hospitalization, morbidity, and/or mortality. Therefore, these patients are also candidates for cellular cardiomyoplasty.

In certain embodiments, the treatment with cellular cardiomyoplasty involves both the implantation with cells and the administration of a pro-angiogenic factor (or vector encoding a pro-angiogenic factor). This treatment is described in more detail in U.S. patent application, U.S. Ser. No. 60/666,932, filed Mar. 31, 2005, entitled "Treatment for Heart Disease", which is incorporated herein by reference. Without wishing to be bound by any particular theory, it is hypothesized that by combining cellular cardiomyoplasty with the administration of a pro-angiogenic factor, the cells being transplanted have a better survival rate when compared to treatment with cellular cardiomyoplasty alone. The treatment with pro-angiogenic factor(s) leads to the development of new blood vessels in the ischemic, damaged, or injured area of the heart which will receive the implanted cells. These results combined with cellular cardiomyoplasty may lead to better survival and engraftment of the implanted cells.

Cellular Cardiomyoplasty

If the patient is selected for treatment using cellular cardiomyoplasty as a "bridge to recovery", then cells are implanted into the heart of the patient. Cells are implanted into a diseased or injured area of the heart to improve cardiac function. Cells that are useful in the inventive system include cells that can proliferate and engraft themselves into the existing myocardium of the patient. Cells found to be particularly useful in the inventive system include myoblasts (e.g., skeletal myoblasts), mesenchymal stem cells, fetal cardiomyocytes, embryonic stem cells, and bone marrow stem cells. In certain embodiments, skeletal myoblasts are used in the inventive system. For further discussion of skeletal myoblasts useful in the inventive system, please see U.S. Patent Applications U.S. Ser. No. 60/145,894, filed Jul. 23, 1999; U.S. Ser. No. 09/624,885, filed Jul. 24, 2000; and U.S. Ser. No. 10/105,035, filed Mar. 21, 2002; each of which is incorporated herein by reference. In certain embodiments, cardiomyocytes are used in the inventive system (see, for example, U.S. Pat. Nos. 6,673,604; 6,491,912; 5,919,449; published U.S. Patent Application 2003/0232431; 2003/0022367; 2001/0053354; each of which is incorporated herein by reference). In certain embodiments, the cells administered are a 40%, 50%, 60%, 70%, 80%, 90%, 95%, 98%, 99% pure population of cells. In other embodiments, a pure population of cells is prepared and optionally combined with other cell types before administration to the heart. As discussed in the above referenced applications, the purity of the skeletal myoblast or other cell population may be obtained by culturing cells from a muscle biopsy under certain conditions with 5-20 doublings, preferably 10-15 doublings, or more preferably 11-12 doublings (see Jain et al. *Circulation* 103:1920-1927, 2000; incorporated herein by reference). In certain embodiments, the cells are not cultured. In other embodiments, the cells are minimally cultured. For example, the cells may be left on a cell culture plate for a few minutes, hours, or days followed by removal of non-adherent cells. In certain embodiments, all or a substantial portion of the cells have not undergone cell division before they are administered. In other embodiments, the cells have undergone 1-2 doublings, 3-4 doublings, 4-5 doublings, or 5-10 doublings. The purity of the skeletal myoblasts may be tested by the presence of the CD56 marker or other marker on the cells. In other embodiments the cells are stem cells (e.g., embryonic stem cells, fetal stem cells, adult-derived stem cells, etc.). The cells administered are preferably at least 70%, 75%, 80%, 85%, 90%, 95%, 98%, 99% viable, more preferably at least 90% or 95% viable.

In certain embodiments, the cells are mesenchymal stem cells or cells derived from mesenchymal stem cells. In certain embodiments, cells are treated in a manner which causes them to acquire stem cell qualities. Typically, the cells are immature or undifferentiated, allowing them to differentiate into myocytes after implantation. In certain embodiments, the mesenchymal stem cells are obtained from the bone marrow of the patient. The mesenchymal stem cells may be co-cultured with cardiomyocytes such as fetal cardiomyocytes. The culturing with fetal cardiomyocytes helps to obtain cells that have pre-differentiated towards a cardiac myocyte phenotype. In certain embodiments, the stem cells may fuse with the cardiomyocytes. In other embodiments, this fusion is to be avoided. In certain embodiments, the cells are not cultured at all or are minimally cultured as described above.

The cells used in the inventive system can be obtained from any source. However, the cells are typically harvested from the patient so that there are no rejection issues (i.e., autologous transplantation). The cells, for example, may be harvested from the muscle of the patients, from the bone marrow, from the blood, from the fetal cord blood of the patient, etc. Besides autologous transplantation, the cells may be obtained from a relative, an MHC-matched donor, a donor of the same blood type, or any donor of the same species. In certain embodiments, cross-species donation of cells is used (i.e., xenogenic transplantation). As would be appreciated by a treating physician, immunosuppression may be required if the donor cells are not from the patient or a related donor. The cells may also be treated or modified to reduce their immunogenicity. For example, the MHC class I molecules on the cells may be masked or modified to limit their immunogenicity.

In general, at least about 50%, 60%, 70%, 80%, 90%, 95%, 98%, or 99% of cells in a population should be viable (as determined by such methods as Trypan Blue exclusion) in order for the population to be useful in accordance with the present invention. Typically, the cell viability immediately before administration is greater than 90%, 95%, or 98%. The number of cells administered may range from $1 \times 10^4$ to $1 \times 10^{10}$ cells, or $1 \times 10^5$ to $1 \times 10^9$ cells, or $1 \times 10^6$ to $1 \times 10^8$ cells, or $1 \times 10^6$ to $1 \times 10^{10}$ cells, or $1 \times 10^7$ to $1 \times 10^8$ cells, or $1 \times 10^8$ to $1 \times 10^9$ cells. The cells may all be injected at one site or multiple sites (e.g., 3 to 30 sites). Typically, 10 million cells are administered per injection. The total number of cells administered will depend on the extent of damaged cardiac tissue. The cells are typically injected into the myocardium between the endocardium and epicardium over a 1-5 cm distance.

The cells used in the invention may also be genetically engineered. The cells may be engineered using any techniques known in the art. For example, the genomes of the cells may be altered permanently, or the cells may be altered to express a gene only transiently. In certain embodiments, the cells are genetically engineered to produce a pro-angiogenic peptide or protein as described in U.S. application U.S. Ser. No. 60/666,932, filed Mar. 31, 2005, entitled "Treatment for Heart Disease." In certain embodiments, the implantation of cells engineered to express at least one pro-angiogenic factor constitutes both the administration of a pro-angiogenic agent and implantation of cells. The angiogenic peptide/protein may be expressed constitutively in the transplanted cells, or it may be expressed upon a certain stimulus. Certain stimuli that may control gene expression include hypoxia, lack of nutrients, presence of growth factors, change in pH, build up of waste products, cell stress, etc. In certain embodiments, the transplanted cells of the invention may express an anti-apoptotic gene. In other embodiments, the cells express or can be induced to express a gene to increase proliferation such as a growth factor (e.g., basic fibroblast growth factor (bFGF)). In other embodiments, a cardiac cell phenotype is promoted in the cells by expressing a cardiac cell gene product in the cell. For example, the GATA transcription (e.g., GATA4, GATA6) may be expressed in the cells in order to promote the cardiac cell phenotype.

The cells are delivered into the injured tissue using any technique known in the art. The cells may be delivered during heart surgery. Alternatively or additionally, the cells may be delivered via a catheter. The cells are typically injected into the injured tissue using a syringe and needle. In certain embodiments, a side port needle is used to inject the cells into the tissue (see U.S. Patent Applications U.S. Ser. No. 60/401,449, filed Aug. 6, 2002, and U.S. Ser. No. 10/635,212, published as US 2004/0191225, filed Aug. 6, 2003; each of which is incorporated herein by reference).

Due to the force of the contracting heart, it may be desirable to take steps to limit the number of cells that escape from the injection site in the myocardium. For example, pressure can be applied at the injection site for seconds to minutes after the needle has been removed. Alternatively or additionally, a viscosity enhancing agent, such as a matrix may be utilized, e.g., being combined with the cells prior to injection. The matrix may be a biocompatible polymer (e.g., cellulose, protein, polyethylene glycol, sorbitol, poly(lactic-glycolic acid), etc.) or other excipient such as glycerol, carbohydrates, etc. In certain embodiments, the polymer is also biodegradable. In some embodiments, the polymer is a biomatrix (e.g., a protein, ECM protein). In some embodiments, the polymer is a biogel. In certain embodiments, the matrix is Cymetra. In certain other embodiments, the matrix is a decellularized dermal matrix, preferably a decellularized dermal matrix. The matrix may also be a basement membrane matrix. The matrix may be impreganated with pro-angiogenic factor in certain embodiments. The matrix can be selected to allow for delayed release (e.g., over time and/or in response to a signal or environmental trigger) of pro-angiogenesis factor. In other embodiments, a plug (e.g., a polymeric plug) or bandage (e.g., suture) may be applied over the injection site to prevent the efflux of injected cells.

The inventive method may be repeated as determined by a treating physician. Certain steps of the method may be repeated. For example, a pro-angiogenic factor may be administered repeatedly, or cells may be transplanted repeatedly, or both. The disease and condition of the patient may be used in determining the extent to which repeat therapy is warranted. As described above, the inventive method may be combined with more traditional treatments such angioplasty, coronary artery bypass graft, left ventricular assist device, drug therapy, stent placement, heart transplant, etc.

The inventive system is designed to improve the cardiac function of the patient, stabilize cardiac function, and/or limit the decrease in cardiac function. In certain embodiments, the inventive system may improve cardiac function by 1%, 2%, 5%, 10%, 20%, 30%, 40%, 50%, 75%, 100%, 200%, 300%, 400%, or 500% as measured by any number of parameters including ejection fraction, stroke volume, cardiac output, blood pressure, etc. These parameters may be measured by echocardiography, MRI, catheterization, EKG, blood pressure cuff, pulse oximeter, etc. In certain embodiments, the improvement in cardiac function may be measured by exercise tolerance test. In certain embodiments, the inventive system prevents the dilatation and/or weakening of the heart, especially after ischemic injury to the heart. In certain embodiments, the inventive system maintains the left ventricular end-systolic index at greater than 50 mL/m$^2$, at greater than 60 mL/m$^2$, or at greater than 70 mL/m$^2$. In certain embodiments, left ventricular dilatation is decreased or stabilized. In certain embodiments, mid-papillary short axis length is decreased. In certain embodiments, the inventive system is used to stabilize the patient before another treatment is performed such as heart transplantation. Preferably, "bridge to recovery" treatment of a patient results in a patient being able to live a lifestyle similar to the one led by the patient before a cardiac event such as an MI. For example, the patient is able to walk the same distance or the exercise the same amount as before the cardiac event. In certain embodiments, the patient no longer needs hospitalization, by-pass surgery, angioplasty, stent placement, or cardiac transplantation. In certain embodiments, patient mortality is decreased.

The inventive system may be combined with other treatment modalities. These other treatments include medication (e.g., blood pressure medication, calcium channel blockers, digitalis, anti-arrhythmics, ACE inhibitors, anti-coagulants, immunosuppressants, pain relievers, vasodilators, etc.), angioplasty, stent placement, coronary artery bypass graft, cardiac assist device (e.g., left ventricular assist device, balloon pump), pacemaker placement, heart transplantation, etc.

In certain embodiments, the inventive system provides a bridge to recover for a patient waiting to undergo heart transplantation.

Kits

The present invention also provides kits useful for the practice of the inventive system. The kit typically contains any combination of equipment, apparatus, pharmaceuticals, biologicals, reagents, medical devices, cells, etc. useful in the practice of the invention. The contents of the kit are conveniently packaged for a treating physician, nurse, or other medical personnel to use. The materials in the kit may also be packaged under sterile conditions. In certain embodiments, the kit may contain any or all of the following: cells, syringes, catheters, needles (e.g., side port needles), media, buffers, angiogenic factors, vectors for expressing angiogenic factors (e.g., VEGF or any other factor described above), adenoviral vectors, storage containers, vials, anesthetics, antiseptics, instructions, polynucleotides, bandages, pharmaceutically acceptable excipient for delivering cells, tissue culture plates, enzymes, antibodies, etc.

In certain embodiments, a kit is provided for selecting a patient for treatment with cellular cardiomyoplasty as a "bridge to recovery." The kit may include reagents and tools for performing various tests including blood tests, unrinanalysis, etc. The kit may include software or instructions for selecting a patient. The kit may also include the materials for treating the patient if he or she is selected as a patient for treatment.

In certain embodiments, a kit is provided for harvesting skeletal myoblasts from the patient, purifying the cells, and expanding the cells. Such a kit may include any of the following: needles, syringes, buffers, cell culture media, serum, storage media, glycerol, cell culture dishes, instruction manual, and combinations thereof. The kit may also include material for purifying cells. The kit may also contain materials for detecting the purity of the resulting population (e.g., antibodies directed to a cell marker).

In another embodiment, a kit is provided for practicing the treatment method. The kit may include any of the following: needles, catheters, syringes, angiogenic factors, vectors for expressing angiogenic factors, pharmaceutically acceptable excipient for injecting cells, instruction manual, and combinations thereof. In certain embodiments, the kit includes a purified angiogenic factor such as VEGF. The factor may be supplied as a lyophilized powder.

The invention also provides other materials and reagents which may be included in the kits as described above. For example, the invention provides vectors and polynucleotides useful in the present invention. In certain embodiments, the vector is a genetically engineered adenovirus. In certain particular embodimetns, the vector is a genetically engineered adenovirus which leads to the expression of VEGF in cell it infects. The vector may also include control sequences for controlling the expression of the angiogenic factor. For example, the expression of the angiogenic factor may be induced a lack of oxygen, change in pH, build-up of waste products, etc. The vector may also contain sequences for replicating and selecting the vector.

The invention also provides cells for the inventive system. Typically, these cells are myoblasts (e.g., skeletal myoblasts), fetal cardiomyocytes, embryonic stem cells, and bone marrow stem cells. In certain preferred embodiments, the cells are skeletal myoblasts. The cells may be genetically engineered. In particular, the cells may be genetically engineered to express an angiogenic factor. In other instances, the cells may express an anti-apoptotic gene to prevent the cells from undergoing apoptosis. In certain embodiments, the cells are purified away from other cells or from other components the cells are normally found with.

These and other aspects of the present invention will be further appreciated upon consideration of the following Examples, which are intended to illustrate certain particular embodiments of the invention but are not intended to limit its scope, as defined by the claims.

EXAMPLES

Example 1

Correlation of Autologous Skeletal Myoblast Survival with Changes in Left Ventricular Remodeling in Dilated Ischemic Heart Failure Introduction Autologous skeletal myoblast (ASM) transplantation, or cardiomyoplasty, has been shown in multiple experimental studies to improve cardiac function after myocardial infarction (MI) (Chiu et al. "Cellular cardiomyoplasty: myocardial regeneration with satellite cell implantation" *Ann. Thor. Surg.* 60:12-18, 1995; Li et al. "Cardiomyocyte transplantation improves heart function" *Ann. Thor. Surg.* 62:654-61, 1996; Murry et al. "Skeletal myoblast transplantation for repair of myocardial necrosis" *J Clin. Invest.* 98:2512-23, 1996; Scorsin et al. "Comparison of effects of fetal cadiomyocyte and skeletal myoblast transplantation on postinfarction left ventricular function" *J. Thor. Cardiovasc. Surg.* 119:1169-75, 2000; Tambara et al. "Transplanted skeletal myoblasts can fully replace the infarcted myocardium when they survive in the host in large numbers" *Circulation* 108[suppl II]:II-259-63, 2003; Taylor et al. "Regenerating functional myocardium: improved performance after skeletal myoblast transplantation" *Nat. Med.* 4(8):929-33, 1998; Jain et al. "Cell therapy attenuated deleterious ventricular remodeling and improves cardiac performance after myocardial infarction" *Circulation* 103:1920-1927, 2000; each of which is incorporated herein by reference). Though the majority of studies have been performed in small animal models of MI, there is evidence of similar improvement in larger animal models (Ghostine et al. "Long-term efficacy of myoblast transplantation on regional structure and function after myocardial infarction" *Circulation* 106[suppl I]:I131-6, 2002; incorporated herein by reference) and in the first patient trials (Menasche et al. "Myoblast transplantation for heart failure" *Lancet* 357:279-80, 2001; Menasche et al. "Autologous skeletal myoblast transplantation for severe postinfarction left ventricular dysfunction" *J. Am. Coll. Cardiol.* 41:1078-83, 2003; Pagani et al. "Autologous skeletal myoblasts transplanted to ischemia-damaged myocardium in humans" *J. Am. Coll. Cardiol.* 41:879-888, 2003; Pouzet et al. "Factors affecting functional outcome after autologous skeletal myoblast transplantation" *Ann. Thorac. Surg.* 71:844-851, 2001; each of which is incorporated herein by reference). The mechanism behind such positive functional changes remains poorly understood given that developing and engrafted skeletal myoblasts are electro-mechanically isolated from their host myocardium (as evidenced by the lack of connexin43 and/or gap junctions (Scorsin et al. "Comparison of effects of fetal cadiomyocyte and skeletal myoblast transplantation on postinfarction left ventricular function" *J. Thor. Cardiovasc. Surg.* 119:1169-75, 2000; Ghostine et al. "Long-term efficacy of myoblast transplantation on regional structure and function after myocardial infarction" *Circulation* 106[suppl I]:I131-6, 2002; Menasche et al. "Myoblast transplantation for heart failure" *Lancet* 357:279-80, 2001; Menasche et al. "Autologous skeletal myoblast transplantation for severe postinfarction left ventricular dysfunction" *J. Am. Coll. Cardiol.* 41:1078-83, 2003; Pouzet et al. "Factors affecting functional outcome after autologous skeletal myoblast transplantation" *Ann. Thorac. Surg.* 71:844-851, 2001; each of which is incorporated herein by reference). Furthermore, clinical ASM cardiomyoplasty has been applied exclusively to patients with severe ischemic cardiomyopathy, and more importantly, it has always been performed as an adjunct to coronary revascularization and/or left ventricular assist devices (LVADs) (Pagani et al. "Autologous skeletal myoblasts transplanted to ischemia-damaged myocardium in humans" *J. Am. Coll. Cardiol.* 41:879-888, 2003; incorporated herein by reference). Because of these concomitant therapies, the improvements in indices of myocardial perfusion, viability and function may be difficult to attribute to ASM injection alone.

Additionally, growing experimental evidence suggest that the number of ASM cells transplanted and the functional/geometrical impacts are directly related (Tambara et al. "Transplanted skeletal myoblasts can fully replace the infarcted myocardium when they survive in the host in large numbers" *Circulation* 108[suppl II]:II-259-63, 2003; Pouzet et al. "Factors affecting functional outcome after autologous skeletal myoblast transplantation" *Ann. Thorac. Surg.* 71:844-851, 2001; each of which is incorporated herein by reference). For example, Tambara et al. ("Transplanted skeletal myoblasts can fully replace the infarcted myocardium when they survive in the host in large numbers" *Circulation* 108[suppl II]:II-259-63, 2003; incorporated herein by reference) using fetal-derived ASM in rats demonstrated that both cardiac function and remodeling were impacted in a dose dependent fashion. However, these benefits have not been demonstrated in ischemic dilated HF, where elevated wall stresses and altered myocardial mechanoenergetics could compromise ASM survival, differentiation, and ultimately functional efficacy. Thus, the aims of the present study were to evaluate LV remodeling and function after ASM transplantation into an animal model of end-stage ischemic HF (LVEF<35% and LV end-systolic volume>80 ml/m$^2$). Furthermore the study also sought to evaluate the survival, differentiation and alignment of ASM injected into those same animals.

Materials and Methods

Ischemic Heart Failure Model

Experimental ischemic heart failure was created in sheep as Sabbah et al ("A canine model of chronic heart failure produced by multiple sequential coronary microembolizations" *Am. J. Physiol.* 260:H 1379-84, 1991; incorporated herein by reference) described in dogs with minor modifications. Briefly, serial and selective left circumflex coronary artery (LCxA) microembolizations (2.9±0.4 injections per animal) were performed by injecting polystyrene beads (70-110 µm) weekly until the left ventricular ejection fraction (LVEF) was maintained at or below 35% for 2 consecutive weeks.

Experimental Groups

The HF control group of sheep (baseline) was instrumented 2 weeks prior to LCxA microembolizations and HF induction (HF control, N=6). The transplanted group of sheep had LCxA microembolization and HF induction prior to instrumentation and injection with ASM (HF+ASM, N=5). Studies were performed weekly for 6 weeks in awake and unsedated animals.

Chronic Instrumentation

All sheep were instrumented through a left thoracotomy; a left ventricular (LV) solid-state electronic pressure transducer (4.0 or 4.5 mm, Konigsberg, Calif.) was placed into LV at its apex and chronic, heparinized (1000 U/mL) fluid filled catheters (Tygon) were inserted for monitoring of aortic, LV, and right ventricular (RV) pressures. Six piezoelectric crystals (Sonometrics Inc., New London, Ontario Canada) were surgically placed in the LV endocardium at the mid papillary level (short axis, SA), at the LV base and apex (long-axis, LA) and in the mid myocardium of the posterolateral LV (segment length, $SL_{post}$). A 16 mm occluder (In Vivo Metrics. Healdsburg, Calif.) was positioned around the inferior vena cava (IVC). All catheters and cables were tunneled to positions between the animals' scapula.

Hemodynamic Measurements and Pressure Volume Analysis

Aortic, RV, and LV fluid-filled catheters were attached to calibrated Statham pressure transducers (Model: P23XL; Biggo-Spectramed, Ocknard, Calif.) and amplified (Gould, Valley, Ohio). The electronic LV pressure gauge was calibrated using the LV fluid-filled catheter. Pressures waveforms were collected (at 1 kHz) and analyzed by a 16-channel data acquisition and software system (IOX; EMKA Technologies, Falls Church, Va.).

Sonometric signals were analyzed for waveform cardiac-cycle dependent (end-diastolic and end-systolic) and independent (minimum, maximum, mean etc) parameters. Left ventricular volume (ml) was calculated in real-time using SA and LA dimensions and the following equation: $SA^2*LA*\pi/6/1000$. Left ventricular volume indices were calculated: LV volume*body surface area (ml/m$^2$). Inferior vena cava occlusions were performed for the generation of PV relationships that were analyzed off-line with analysis software (IOX, EMKA).

Left ventricular work was estimated (Todaka et al. "Characterizing ventricular mechanics and energetics following repeated coronary microembolizations" *Am. J. Physiol.* 272:H 186-94, 1997; Suga, "Ventricular Energetics" *Physiol. Rev.* 70:247-77, 1990; each of which is incorporated herein by reference) by calculating the pressure volume area (PVA). PVA was calculated from off-line ESPVR-derived data as the sum of the LV potential energy ($PE_{LV}$) and stroke work ($SW_{LV}$).

$$PE_{LV}=(\tfrac{1}{2}[V_0-LVESV]\times LVESP)$$

$$PVA=SW_{LV}+PE_{LV}$$

$V_0$: volume of the LV at zero pressure x-intercept of $E_{es}$), LVESV: LV end-systolic volume (mL) and LVESP: LV end-systolic pressure.

Skeletal Muscle Biopsy and Autologous Skeletal Myoblast Culture

Skeletal muscle biopsy (1-3 grams) was harvested from the left forelimb of sheep at the time of the first microembolization in HF+ASM sheep. The forelimb muscle was exposed and the biopsy taken using sharp dissection avoiding electrocautery and placed into a tube containing biopsy transport media and shipped to GenVec, Inc (Charlestown, Mass.) for ASM preparation and culture similar to that described by Jain et al. (Jain et al. "Cell therapy attenuated deleterious ventricular remodeling and improves cardiac performance after myocardial infarction" *Circulation* 103:1920-1927, 2000; incorporated herein by reference).

All cells were expanded for 11-12 doublings and cryopreserved prior to transplant. The myoblasts were thawed, formulated in Transplantation Media, and shipped for direct myocardial injection. Myoblast purity was measured by reactivity with anti-NCAM mAb (CD56-PE, Clone MY-31, BD Biosciences, San Diego, Calif.) and by the ability to fuse into multinucleated myotubes. Cell viability was determined by Trypan Blue exclusion. Myoblasts were loaded into tuberculin syringes (~$1.0\times10^8$ cells/mL) and shipped at 4° C. At the time of transplant, cells were allowed to warm slowly to room temperature, resuspended by gentle agitation and injected without further manipulation. Autologous skeletal myoblasts were injected at multiple sites in the infarcted myocardium in proximity to segmental sonomicrometry crystals. To avoid inadvertent intravascular or intraventricular injection of cells, the injection needle was passed into the mid myocardium equidistant from the epi- and endocardial surfaces over a 3-4 cm distance, negative pressure was applied to the syringe and if no blood was returned the cells were injected as the needle was slowly withdrawn. Slight pressure was applied over the needle exit site for several seconds after injection to limit cell efflux from the needle track.

Histology

After six weeks of study, each animal was euthanized, the heart removed, and perfused with 10% buffered formalin. Tissue blocks were made from embolized myocardium receiving ASM injection. Hematoxylin and eosin and Trichrome stains were performed using standard methods.

Immunohistochemistry

Deparaffinized sections were stained immunohistochemically with an anti-myosin heavy chain antibody that does not react with cardiac muscle, alkaline phosphatase-conjugated MY-32 mAb (Sigma, St Louis, Mo.), to confirm the phenotype of the mature grafts. Sections were developed with BCIP-NBT (Zymed Lab Inc., San Francisco, Calif.) and counter stained with nuclear red. Additionally stains for connexin-43 Ab (Chemicon, Temecula, Calif.), and cardiac specific troponin I (Chemicon) were performed.

Estimation of Myoblast Survival

The heart was cut into blocks approximately 2.5 cm×2.5 cm×3 mm in dimension and processed in paraffin. In some cases the whole block was sectioned (5 µm thickness), in other cases, only a portion of the tissue was sectioned. For performing quantitative cell counts, tissue sections were then immunostained for skeletal-specific myosin heavy chain (MY-32). Cell viability at 6 weeks was assumed based on the initiation of myosin heavy chain expression (Havenith et al. "Muscle fiber typing in routinely processed skeletal muscle with monoclonal antibodies" *Histochem.* 93:497, 1990; incorporated herein by reference), cytoarchitectural organization consistent with skeletal myocytes, and the presence of normal appearing nuclei located peripherally. Using representative tissue sections and computer-assisted imaging analysis, the areas of engraftment were calculated and converted to the number of engrafted nuclei according to a separate count of nuclei density performed on Trichrome stained sections. The total number of surviving myoblast nuclei in each tissue block was estimated using the following equation:

Sum of Graft Area in Secftion×Density of Nuclei Per Graft Area×#Sections Per Block*×Abercrombie Correction

*Estimated number of sections per block according to approximate block thickness of 3 mm and section thickness of 5 µm.

(Abercrombie, "Estimation of nuclear population from microtome sections" *Ant. Rec.* 94:239-47, 1946; incorporated herein by reference)

Statistical Analysis

Data are presented as mean±standard error of mean (SEM). The differences over time and between groups for LV hemodynamic, geometric, and functional data during the 6-week HF study period were studied using multifactoral (two-way) analysis of variance (ANOVA) with repeated measurements (factors: group and time). For HF control, the differences between baseline and HF time points were established using a one-way ANOVA test with repeated measurements. If the F-ratio exceeded a critical value (alpha<0.05) the post-hoc Student-Newman-Keuls method was used to perform pairwise comparisons. HF+ASM data at HF week 1 was compared to baseline using a t-test.

Individual regression analysis for PV relationships was computed by analysis software (IOX, EMKA Technologies). The equality of the PV relationships for the HF+ASM and HF controls was studied with multiple-linear regression considering both qualitative (group) and interaction terms, i.e. simultaneously testing the differences in slope and intersect of the regression functions. Linear regression analyses were also performed to study the relationship between indices of LV remodeling and function versus the number of surviving ASM-derived myocytes including HF controls (N=11).

In establishing HF as both an increased ESVI and decreased LVEF, a null hypothesis consisting of two variables, a Bonferroni method for multiple comparisons was used with an appropriate level of confidence: alpha<0.025. P-values were determined and considered in assigning significance and importance of comparisons.

Results

Eleven sheep were studied for six weeks after establishment of HF with ASM injection (HF+ASM, N=5) or without (HF control, N=6). Three of 8 sheep intended for the HF+ASM group died during the instrumentation procedure; either before ASM injection (N=2) or within 72 hours after injection, and were not included in the study. No sheep in the HF controls died early. Animals had maintenance of appetite and weight over the six-week study. Sheep were less active after HF induction and dyspneic upon mild exertion, but no differences in daily observations were appreciated between groups.

Histology

The average number of injected myoblasts was $3.44\pm0.49\times10^8$ cells, ranging from 1.53 to $4.3\times10^8$ cells. Myoblast purity, $92\pm1.4\%$, and cell viability, $93\pm1.2\%$, were assessed at the time of transport and myoblast viability was confirmed to be >90% (using trypan blue exclusion) after shipment (4° C.). ASM-derived skeletal myofibers were found in all injected hearts, but the relative survival (see discussion) of injected myoblasts surviving at week 6 ranged from 140,000 cells (0.05% survival) to 33 million cells (10.7% survival).

Figure 2:
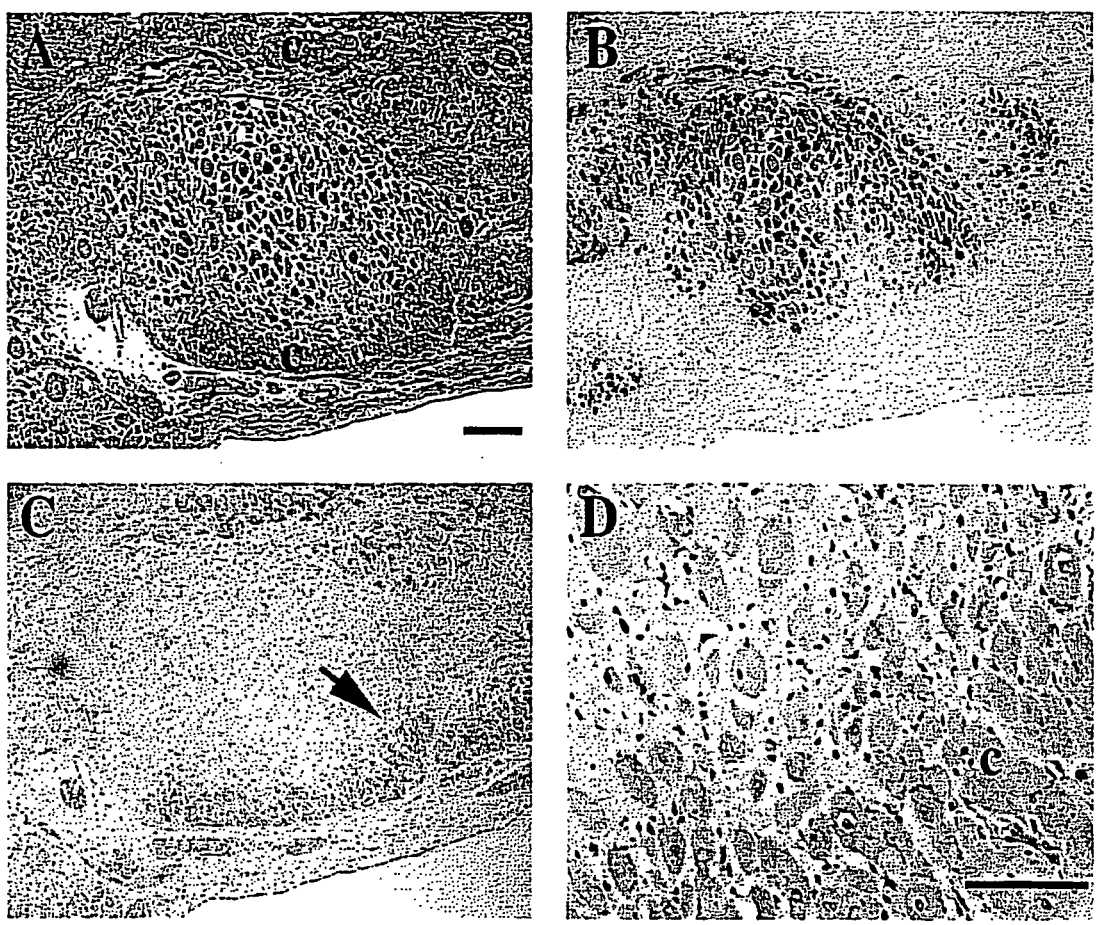
FIG. 2 shows viable muscle within an area of myocardial fibrosis and scar as seen with Trichrome staining (A). Staining with MY-32 (B) confirmed that ASM-derived skeletal muscle engrafted in close proximity and aligned with remaining cardiac myocytes ('c') did not selectively stain for tropinin-I (C). At higher magnification from the same area (C, arrow), ASM-derived skeletal myocytes do not stain for connexin43 (D) despite very close apposition to remaining cardiac myocytes ('c'). Scale bars in panels A and D are 0.2 mm and 0.1 mm, respectively.

Representative histological sections with detailed descriptions are found in FIGS. 1 and 2. In general, skeletal myocytes were seen aligned with other skeletal muscle fibers as well as aligned with remaining cardiac myocytes (FIG. 1C-F; FIG. 2A, B). Engrafted skeletal muscle fibers were characterized by staining to the myosin heavy chain fast-twitch isoform (purple staining FIGS. 1B, D, F and 2B). However, in no section were ASM-derived myofibers seen stained for troponin I or connexin-43 despite close apposition to surviving cardiac myocytes (FIGS. 2C & D, respectively).

Cardiac Hemodynamics

Hemodynamic data are summarized in Table 1. The study was adequately powered ($\beta\leq0.20$) to detect a 50% change in LVEF; however, no animal had improvement in $dP/dT_{max}$ or LVEF after ASM injection. No linear relationship was found between the number of surviving cells and LVEF ($R^2=0.00017$, $p=0.99$) or dP/dTmax ($R^2=0.048$, $p=0.543$).

TABLE 1

Cardiac Hemodynamics after Autologous Skeletal Myoblast Transplantation

| | | Baseline (N = 6) | HF Ctrl Wk 1 (N = 6) | HF Ctrl Wk 6 (N = 6) | ASM + HF Wk 1 (N = 5) | ASM + HF Wk 6 (N = 5) |
|---|---|---|---|---|---|---|
| Heart Failure | ESVI ml/m² | 39 ± 4 | 93 ± 7* | 124 ± 15‡§ | 85 ± 16* | 98 ± 18§ |
| | LVEF % | 48 ± 2 | 30 ± 2* | 28 ± 2 | 29 ± 4* | 27 ± 4 |
| | HR bpm | 109 ± 4 | 126 ± 7* | 125 ± 9 | 128 ± 9* | 110 ± 10‡ |
| | LVSP mmHg | 106 ± 6 | 103 ± 5 | 102 ± 7 | 103 ± 2 | 106 ± 4 |
| | LVEDP mmHg | 11 ± 1 | 23 ± 4* | 26 ± 3 | 21 ± 2* | 22 ± 3 |
| | EDVI ml/m² | 75 ± 7 | 135 ± 9* | 170 ± 15‡§ | 118 ± 16* | 131 ± 2§ |
| | $dP/dT_{max}$ mmHg/sec | 3414 ± 92 | 2428 ± 327* | 1864 ± 216‡ | 2863 ± 152* | 2166 ± 174‡ |
| | $dP/dT_{min}$ mmHg/sec | −2124 ± 108 | −1582 ± 173* | −1423 ± 147 | −1880 ± 68* | −1713 ± 84 |
| | Tau ms | 17 ± 1 | 38 ± 8* | 39 ± 4 | 34 ± 4* | 44 ± 3‡ |
| Pressure Volume Analysis HF + ASM (N = 4), HF ctrl (N = 5) | $E_{es}$ | 3.7 ± 0.5 | 1.3 ± 0.11* | 0.9 ± 0.13 | 1.6 ± 0.22 | 1.6 ± 0.28 |
| | $V_o$ | 18 ± 3.9 | 39 ± 7.8* | 59 ± 8.7‡ | 32 ± 3.1 | 25 ± 3.4§ |
| | $M_w$ | 97 ± 7.4 | 66 ± 10.1* | 58 ± 7.8‡ | 67 ± 5.9* | 57 ± 8.0‡ |
| | $V_w$ | 50 ± 9.5 | 88 ± 4.9*§ | 107 ± 15‡§ | 75 ± 33*§ | 71 ± 2.9§ |
| | PVA | 5257 ± 542 | 6943 ± 856 | 8794 ± 449‡ | 6456 ± 492 | 6900 ± 497 |
| | PE | 1347 ± 165 | 2982 ± 381* | 4304 ± 375‡ | 2791 ± 437* | 3208 ± 500 |
| | SW | 3910 ± 433 | 3961 ± 542 | 4489 ± 710 | 3675 ± 185 | 3688 ± 541 |

Mean ± SEM.
*p < 0.05 from baseline at week 1.
‡p < 0.05 from week 1 within groups.
§p < 0.05 between groups at respective times.
dP/DT: derivative of pressure,
HR: heart rate,
LVSP: LV systolic pressure,
LVEDP: LV end-diastolic pressure,
ESVI and EDVI: LV end-systolic and diastolic volume index,
Tau: time constant of relaxation (Weiss method).
$M_w$: preload recruitable stroke work;
$E_{es}$: end-systolic pressure volume relationship;
Vo: x-intercept of $E_{es}$;
$V_w$: x-intercept of $M_w$;
PE: potential LV energy,
SW: LV stroke work.

Pressure Volume Analysis (PV Analysis)

Figure 3:
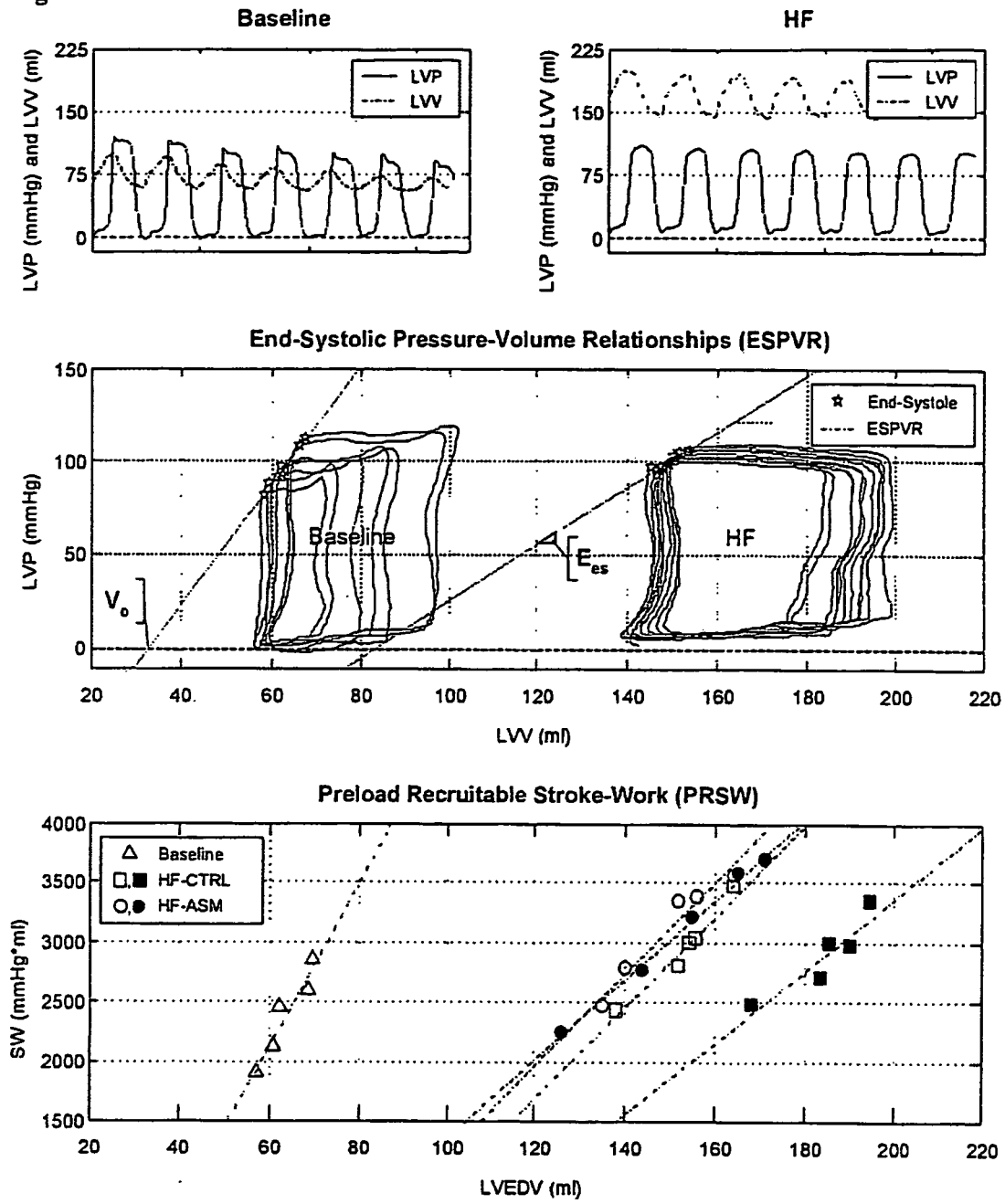
FIG. 3 represents left ventricular volume (LVV) and pressure (LVP) tracings from a single sheep before and after microembolization (top and middle panels); highlight changes in the ESPVR (middle) and the PRSW (bottom, squares) with or without ASM transplantation (bottom panel, circles) after microembolization. Though ASM transplantation did not improve cardiac function (slope) after week 1 (○ and ☐), transplantation did prevent a rightward shift in the PRSW seen in the HF control animal at week six (● and ■).

Data for ESPVR, PRSW and LV work (PVA) from HF controls and HF+ASM sheep are summarized in Table 1 and exemplified in FIG. 3. PV analysis demonstrated a decrease in slope of the PRSW ($M_w$) and the load-independent index of cardiac contractility, $E_{es}$, in both groups of HF sheep from baseline. Additional multiple linear regression analyses accounting for covariance between groups also demonstrated no significant differences in slope (WK1: p=0.614, WK6: p=0.519, power=1) or intercept (WK 1: p=0.945, WK6: p=0.928, power=1) of the volume-adjusted PV-relationship were found at any time-point. No linear relationship found between the number of surviving cells and $E_{es}$ ($R^2$=0.088, p=0.436) or $M_w$, ($R^2$=0.0 18, p=0.731).

There was an increase (rightward shift, p=0.026) in the $V_0$ x-intercept of the $E_{es}$ for the HF controls from week 1 to week 6 (FIG. 3). Conversely, for the HF+ASM sheep, the $V_0$ tended (p=0.20) to decrease (leftward shift) over the six weeks in the HF+ASM animals, and a difference was noted (p=0.014) between HF control and HF+ASM at week six, supporting that ASM injection attenuated LV remodeling. As a result and suggesting a greater loss of myocardial efficiency in HF controls, the PE was increased (p=0.028) in the HF controls from week 1 to week 6, though total LV work (PVA) was not different between groups over the 6-week study. Similar to the $V_0$, the x-intercept of the PRSW ($V_w$) was increased from week 1 to week 6 in the HF control group (p=0.03), and remained different (p=0.009) as compared to the HF+ASM group at week 6 (Table 1 and FIG. 3).

Sonomicrometry and Left Ventricular Segmental Function

Left ventricular regional and segment data are presented in Table 2. $SL_{post}$ was not different in either group from week 1, but was increased (p<0.05 at HF Week 1) from baseline in the HF control group. Left ventricular segmental dyskinesia was present after microembolization, therefore, both systolic bulging (SB) and post-systolic shortening (PSS) were evident in both groups throughout the 6-week study.

TABLE 2

Left Ventricular Regional & Segmental Function after Autologous Skeletal Myoblast Transplantation

|  | Baseline (N = 6) | HF Ctrl Wk 1(N = 6) | HF Ctrl Wk 6 (N = 6) | HF + ASM Wk 1(N = 5) | HF + ASM Wk 6 (N = 5) |
|---|---|---|---|---|---|
| $SA_{ES}$ (mm) | 37.9 ± 2.5 | 51.8 ± 2.9* | 57.6 ± 3.6‡ | 51.5 ± 4.9* | 53.4 ± 4.9 |
| SA (% shrt) | 22.3 ± 1.2 | 14.3 ± 2.3* | 13.3 ± 1.7 | 15.2 ± 0.8* | 13.0 ± 1.4 |
| $LA_{ES}$ (mm) | 73.2 ± 3.8 | 83.7 ± 5.2* | 90.2 ± 4.6‡ | 80.4 ± 4.1 | 85.5 ± 4.9 |
| LA (% shrt) | 11.8 ± 0.9 | 9.8 ± 1.1* | 8.5 ± 1.6 | 8.5 ± 0.9* | 8.1 ± 1.9 |
| $SL_{post}$** (mm) | 13.7 ± 3.4 | 17 ± 4.7* | 18.9 ± 5.6 | 12 ± 1.3 | 12.1 ± 1.3 |
| $SL_{post}$ (% shrt) | 7.8 ± 1.6 | −1.6 ± 1.1* | −2.1 ± 1.8 | −1.8 ± 2.2* | −2.4 ± 1.8 |
| SB (mm) | 0.04 ± 0.03 | 0.42 ± 0.10* | 0.53 ± 0.16 | 0.40 ± 0.14* | 0.43 ± 0.18 |
| PSS (mm) | 0.06 ± 0.04 | 0.47 ± 0.13* | 0.61 ± 0.2 | 0.45 ± 0.13* | 0.57 ± 0.12 |

Mean ± SEM.
*p < 0.05 from baseline.
‡p < 0.05 from Wk 1 within groups.
§p < 0.05 between HF control and HF + ASM.
ES: end-systolic,
SA: LV short-axis,
LA: LV long-axis,
$SL_{post}$: posterior LV segment (microembolized),
% shrt: % systolic shortening,
SB: systolic bulging,
PSS: post-systolic shortening.
**note: $SL_{post}$ length differs from baseline to HF ctrl due to regional infarct expansion after instrumentation, whereas HF + ASM does not differ from baseline because instrumentation of HF + ASM animals was after heart failure (after infarct expansion). Therefore, the relevant comparison of groups is from week 1 to week 6.

Sonomicrometry and Left Ventricular Dimensions

Figure 4:
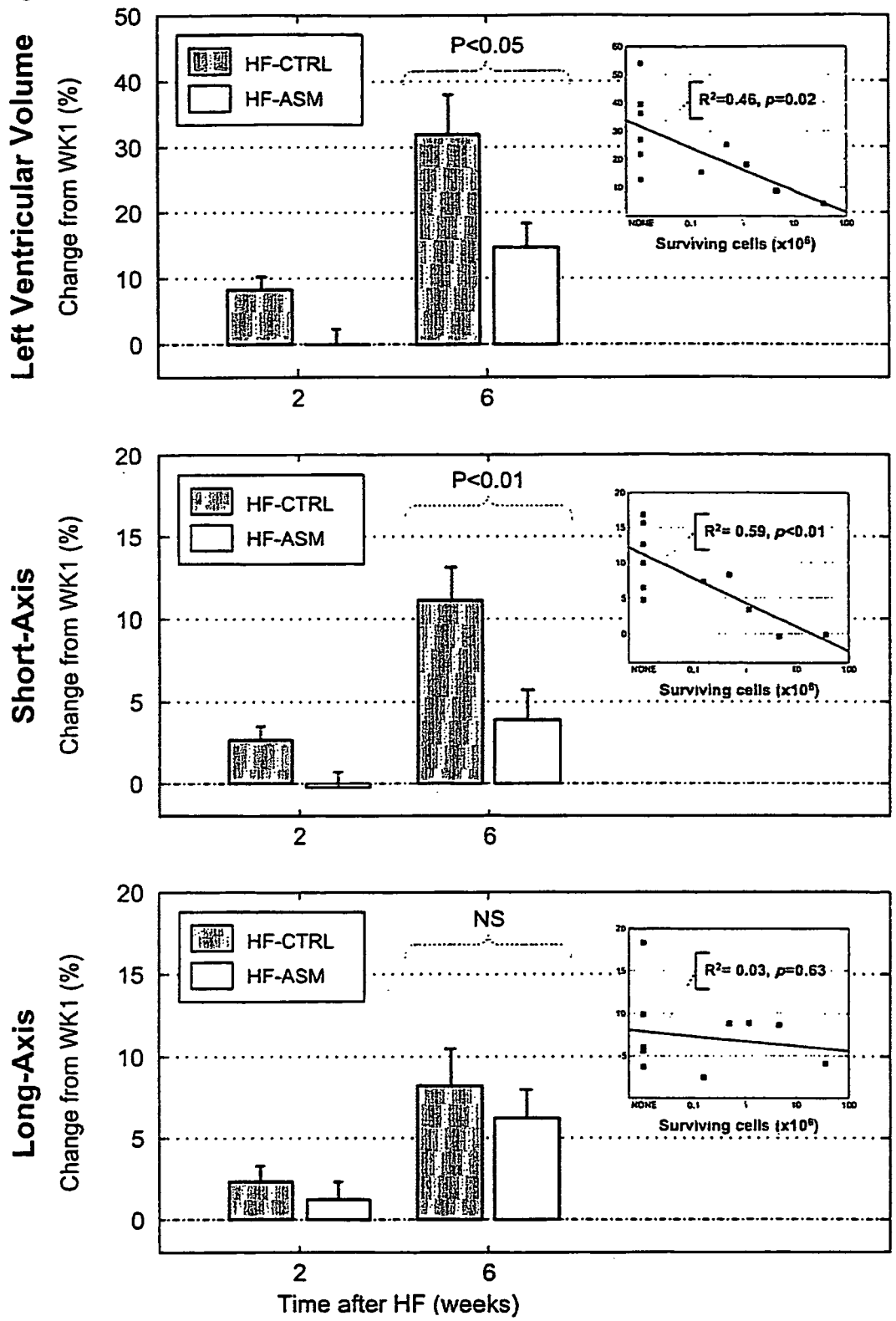
FIG. 4 demonstrates that left ventricular dilatation (ESVI, top panel) and an increase in mid papillary short-axis length (SA, middle panel) were attenuated after ASM injection (N=5, open bars) as compared to heart failure controls (N=6, shaded bars). Left ventricular long-axis length (LA, bottom panel) was not different between groups. All animals, including HF controls ("none"), were used to evaluate the relationship of ASM-derived myocyte survival (log) to that of LV remodeling (inset each panel, N=11). Animals with the highest ASM-derived myocyte survival demonstrated the greatest attenuation, particularly in LV short-axis dilatation. Correlative statistics are presented for each relationship.

Left ventricular end-systolic and end-diastolic volume indexes (ESVI and EDVI, respectively) were increased (p<0.05) from baseline in both groups at HF week 1, however, there was no difference between groups at week 1 (Table 1). In HF+ASM, LV dilatation was attenuated as compared to HF controls (p=0.016) by week 3 (% change in ESVI: 5.3±1.2% and 17.8±3.3%, respectively) and progressed (p=0.006) by week 6 (FIG. 4). The difference in LV volume resulted from a significant (p=0.005) attenuation in SA dilatation alone and also by week 3 in HF+ASM (FIG. 4). No difference (P>0.5) was found in LA dilatation between groups. Correlations of ESVI, SA and LA to ASM survival are presented in FIG. 4.

Discussion

Previous studies have suggested that skeletal myoblasts form viable skeletal muscle grafts that presumably contributed to improved cardiac performance and remodeling after experimental myocardial infarction. Few studies, if any, have examined the impact of ASM in hearts with a pre-existing and clinically significant and severe degree of ischemic dysfunction and remodeling (LVEF<35% with LVESVI>80 ml/m²). The present study establishes the therapeutic benefit of ASM cardiomyoplasty in a clinically applicable model of ischemic, dilated heart failure free of the confounding factors associated with coronary revascularization or other supportive therapies.

ASM-derived skeletal muscle was found in all injected sheep at six weeks. We report here an estimate of survival that allowed the relative survival between animals to be compared. Because significant limitations exist in the method used to calculate cell survival (Abercrombie, "Estimation of nuclear population from microtome sections" *Ant. Rec.* 94:239-47, 1946; incorporated herein by reference), values for cell survival should not be interpreted as absolute cell survival. The long-term survival of myoblasts (up to 10.7% survival) found in this study was higher than reported in patients transplanted with a similar number of ASM cells at the time of LVAD placement (<1% survival) (Pagani et al. "Autologous skeletal myoblasts transplanted to ischemia-damaged myocardium in humans" *J. Am. Coll. Cardiol.* 41:879-888, 2003; incorporated herein by reference). As others have reported (Scorsin et al. "Comparison of effects of fetal cadiomyocyte and skeletal myoblast transplantation on postinfarction left ventricular function" *J. Thor. Cardiovasc. Surg.* 2000; 119:1169-75; Jain et al. "Cell therapy attenuated deleterious ventricular remodeling and improves cardiac performance after myocardial infarction" *Circulation* 103:1920-1927, 2000; Ghostine et al. "Long-term efficacy of myoblast transplantation on regional structure and function after myocardial infarction" *Circulation* 106[suppl I]:I131-6, 2002; Menasche et al. "Myoblast transplantation for heart failure" *Lancet* 357: 279-80, 2001; Menasche et al. "Autologous skeletal myoblast transplantation for severe postinfarction left ventricular dysfunction" *J. Am. Coll. Cardiol.* 41:1078-83, 2003; Pagani et al. "Autologous skeletal myoblasts transplanted to ischemia-damaged myocardium in humans" *J. Am. Coll. Cardiol.* 41:879-888, 2003; Pouzet et al. "Factors affecting functional outcome after autologous skeletal myoblast transplantation" *Ann. Thorac. Surg.* 71:844-851, 2001; each of which is incorporated herein by reference), no staining for connexin-43 was found in ASM-derived skeletal muscle. Transplanted ASM-derived skeletal myofibers aligned with each other and with remaining cardiac myofibers in all sections (FIGS. 1 and 2). Such organized alignment of the ASM-derived fibers suggests that these fibers remained sensitive to stress-strain relationships found within the myocardium (Kada et al. "Orientation change of cardiocytes induced by cyclic stretch stimulation: time dependency and involvement of protein kinases" *J. Mol. Cell. Cardiol.* 31:247-59, 1999; Pfeffer et al. "Ventricular remodeling after myocardial infarction. Experimental observations and clinical implications" *Circulation* 81:1161-72, 1990; Atkins et al. "Intracardiac transplantation of skeletal myoblasts yields two populations of striated cells in situ" *Ann. Thorac. Surg.* 67:124-9, 1999; each of which is incorporated herein by reference). Meaningful estimation of scar replacement after ASM injection was not possible given the heterogeneous infarct pattern present after microembolization and the relatively few animals studied. However, we consistently observed cells surviving aligned with each other in dense myocardial infarct (FIG. 1) and less frequently found cells in close proximity to surviving cardiac myocytes (FIG. 2).

Even with relatively low myoblast cell survival (FIG. 1, animal with 1.1% cell survival), considerable areas of scarred myocardium can be filled with viable myofibers as a result of cell fusion and subsequent enlargement of myofibers (approximately 10-fold increase in myofiber cross-sectional area per nucleus versus myoblasts, unpublished observations). Thus, it may be possible to completely fill damaged areas in the myocardium even with low cellular survival. In general, up to 95% of the injected cells are lost shortly after injection (Menasche, "Myoblast-based cell transplantation" *Heart Failure Reviews* 8:221-27, 2003; Grossman et al. "Incomplete Retention after Direct Myocardial Injection" *Catheterization and Cardiovascular Interventions* 55:392-397, 2002; each of which is incorporated herein by reference). An explanation for this early loss is by means of lymphatic and/or venous drainage of the cells after direct intramyocardial injection (Grossman et al. "Incomplete Retention after Direct Myocardial Injection" *Catheterization and Cardiovascular Interventions* 55:392-397, 2002; incorporated herein by reference). Other factors also likely contribute to the further loss of cells that are retained within the myocardium/scar. Recent, investigations have shown that both the pre-treatment (Retuerto et al. "Angiogenic pre-treatment improves the efficacy of cellular cardiomyoplasty performed with fetal cardiomyocyte implantation" *J. Thorac. Cardiovasc. Surg.* 127:1-11, 2004; incorporated herein by reference) and transfection (Askari et al. "Cellular, but not direct, adenoviral delivery of vascular endothelial growth factor results in the improved left ventricular function and neovascularization in dilated ischemic cardiomyopathy" *JACC* 43:1908-14, 2004; incorporated herein by reference) of ASM with VEGF improved cardiac function, presumably by enhancing perfusion and nutrient delivery. Furthermore, strategies to both limit inflammation and/or apoptosis have also proven beneficial to improving the efficacy after cellular cardiomyoplasty (Zhang et al. "Cardiomyocyte grafting for cardiac repair: graft cell death and anti-death strategies" *J. Mol. Cell. Cardiol.* 33:907-21, 2001; each of which is incorporated herein by reference). No evidence for intense inflammation at the graft sites 6 weeks after injection was observed (FIGS. 1 and 2).

Left Ventricular Function

Data evaluating cardiac performance after ASM injection in Tables 1 and 2 suggests no improvement in any hemodynamic parameter or in index of cardiac contractility in sheep with end-stage, dilated ischemic HF in this model. This discrepancy with results previously published in sheep (Ghostine et al. "Long-term efficacy of myoblast transplantation on regional structure and function after myocardial infarction" *Circulation* 106[suppl I]:I131-6, 2002; incorporated herein by reference) may be due to the worse LV structure and function in our sheep. Ghostine and colleagues improvement in local cardiac function may have been as a result of less severe pathology, and therefore, less of an impediment to ASM contraction if present.

Unlike, Pouzet and colleagues (Pouzet et al. "Factors affecting functional outcome after autologous skeletal myoblast transplantation" *Ann. Thorac. Surg.* 71:844-851, 2001; incorporated herein by reference) who demonstrated in rats stratified for LV function (LVEF) a significant correlation with the number of cells injected to indices of LV function; those most severely impaired received the greatest benefit, we were unable to demonstrate such a relationship compared to the number of surviving ASM-derived myocytes. Beyond the obvious difference in comparing the number of injected cells versus that of the percentage surviving, could this difference be explained by a difference in myoblast culture, expansion or possibly just an insufficient dose of cells? Pouzet et al. and Ghostine et al. present myoblast purity less than 50% at time of injection, whereas we expanded a more pure population of myoblasts (>90% CD56 positive). Could the purity of myoblast injection suspensions impact outcome? Although this is possible, it would seem unlikely that higher myoblast purity would result in diminished functional benefits; moreover, understanding the impact of cell culture and expansion techniques is difficult given the variability in LV pathology in ours and other published animal studies (Ghostine et al. "Long-term efficacy of myoblast transplantation on regional structure and function after myocardial infarction" *Circulation* 106[suppl I]:I 131-6, 2002; Menasche et al. "Myoblast transplantation for heart failure" *Lancet* 357:279-80, 2001; Menasche et al. "Autologous skeletal myoblast transplantation for severe postinfarction left ventricular dysfunction" *J. Am. Coll. Cardiol.* 41:1078-83, 2003; Pagani et al. "Autologous skeletal myoblasts transplanted to ischemia-damaged myocardium in humans" *J. Am. Coll. Cardiol.* 41:879-888, 2003; Pouzet et al. "Factors affecting functional outcome after autologous skeletal myoblast transplantation" *Ann. Thorac. Surg.* 71:844-851, 2001; each of which is incorporated herein by reference).

The lack of a demonstrable direct functional benefit observed in our study may be related to the chronic nature and severity of LV dysfunction in our HF model (multiple microinfarctions over several weeks), as compared to animal models using a single ischemic insult (cryoinfarction (Taylor et al. "Regenerating functional myocardium: improved performance after skeletal myoblast transplantation" *Nat. Med.* 4(8):929-33, 1998; incorporated herein by reference), ligation (Jain et al. "Cell therapy attenuated deleterious ventricular remodeling and improves cardiac performance after myocardial infarction" *Circulation* 103:1920-1927, 2000; incorporated herein by reference), coil embolization (Ghostine et al. "Long-term efficacy of myoblast transplantation on regional structure and function after myocardial infarction" *Circulation* 106[suppl I]:I131-6, 2002; incorporated herein by reference)). The microembolization model may have more effectively exhausted remote myocardial compensatory mechanisms, by design (Sabbah et al. "A canine model of chronic heart failure produced by multiple sequential coronary microembolizations" *Am. J. Physiol.* 260:H1379-84, 1991; incorporated herein by reference), preventing contribution from the remote myocardium after ASM injection. We agree with the interpretation offered by Jain et al. ("Cell therapy attenuated deleterious ventricular remodeling and improves cardiac performance after myocardial infarction" *Circulation* 103:1920-1927, 2000; incorporated herein by reference), in their ex vivo preparation in rats, that modest functional improvements observed after ASM injection were likely the result of benefits to non-functional properties of the LV, i.e., attenuated LV dilatation, rather than directly to LV contraction. In essence, less wall stress placed on remote cardiac myocytes as a result of ASM-derived skeletal muscle preventing further LV chamber dilatation would translate into better remote myocardial function. Perhaps the earlier the treatment the sooner the benefits of ASM-derived skeletal muscle could be realized on LV remodeling, and therefore greater the likelihood that the remote cardiomyocytes could adequately compensate and contribute to global LV function? Likewise, we believe based on our studies that with more severe dilation longer periods may be required for functional changes to be observed.

Left Ventricular Remodeling

An important finding of the present study was the attenuation of LV dilatation after ASM transplantation in a cell survival dependent fashion (FIG. 4). Studies in both large and smaller animals have also shown positive effects on LV dilatation after ASM injection (Tambara et al. "Transplanted skeletal myoblasts can fully replace the infarcted myocardium when they survive in the host in large numbers" *Circulation* 108[suppl II]:II-259-63, 2003; Taylor et al. "Regenerating functional myocardium: improved performance after skeletal myoblast transplantation" *Nat. Med.* 4(8):929-33, 1998; Jain et al. "Cell therapy attenuated deleterious ventricular remodeling and improves cardiac performance after myocardial infarction" *Circulation* 103:1920-1927, 2000; Ghostine et al. "Long-term efficacy of myoblast transplantation on regional structure and function after myocardial infarction" *Circulation* 106[suppl I]:I131-6, 2002; Pouzet et al. "Factors affecting functional outcome after autologous skeletal myoblast transplantation" *Ann. Thorac. Surg.* 71:844-851, 2001; incorporated herein by reference). Another intriguing finding of the current study was that effects on LV dilatation were exclusively for the SA dimension. The mechanism(s) that defines this preferential effect on SA remodeling is not entirely clear. The idea that cellular cardiomyoplasty may be directly impacting scar elasticity and thereby limiting scar expansion is a possible explanation for attenuated regional dilatation (Torrent-Guasp et al. "The structure and function of the helical heart and its buttress wrapping. Articles I-VII" *Semin. Thor. and Cardiovasc. Surg.* 13: 298-416, 2001; incorporated herein by reference). Though the interplay of both post systolic shortening and systolic bulging in chronically ischemic myocardium has not been well characterized (Skulstad et al. "Postsystolic shortening in ischemic myocardium, active contraction or passive recoil" *Circulation* 106:718-24, 2002; incorporated herein by reference), the fact remains that there were no measurable improvements after ASM injection in either PSS or SB.

If ASM-derived skeletal myofibers can actively resist forces (stretch) inline with their fibers, as demonstrated ex vivo (Murry et al. "Skeletal myoblast transplantation for repair of myocardial necrosis" *J. Clin. Invest.* 98:2512-23, 1996; incorporated herein by reference), and thereby limit LV dilatation, this might also explain the observed attenuation to LV dilatation selectively for the LV short axis. For example: as the ventricle becomes increasingly spherical after ischemic injury, the predominate cardiac fiber axis (e.g., 60°) progressively re-orients towards the horizontal or short-axis (e.g., 30°) (Torrent-Guasp et al. "The structure and function of the helical heart and its buttress wrapping. Articles I-VII" *Semin. Thor. and Cardiovasc. Surg.* 13: 298-416, 2001; incorporated herein by reference). We provide evidence that ASM-derived skeletal myofibers were found aligned with each other and with remaining cardiac myocytes and therefore, theoretically, the engrafted ASM-derived myofibers' orientation would be more aligned with the LV short axis. As suggested, ASM-derived myofibers may offer innate resistance to dilatory forces upon or along their fiber lengths, thereby, selectively preventing dilatation aligned with ASM engraftment along the LV short axis (FIG. 4).

Like Jain et al. ("Cell therapy attenuated deleterious ventricular remodeling and improves cardiac performance after myocardial infarction" *Circulation* 103:1920-1927, 2000; incorporated herein by reference), in an isolated heart preparation, we found that ASM cardiomyoplasty prevented a rightward shift of the $E_{es}$ intercept ($V_0$) as well as the intercept for the PRSW (Table 1 and FIG. 4). In light of and in an attempt to meaningfully quantify the apparent discordant effects of ASM transplantation on LV remodeling versus that of LV function, we calculated PVA from acquired pressure volume data (Todaka et al. "Characterizing ventricular mechanics and energetics following repeated coronary microembolizations" *Am. J. Physiol.* 272:H1186-94, 1997; Recchia et al. "Reduced nitric oxide production and altered myocardial metabolism during the decompensation of pacing induced heart failure in the conscious dog" *Cir. Res.* 83(10): 969-79, 1998; Takaoka et al. "Depressed contractile state and increased myocardial consumption for non-mechanical work in patients with heart failure due to old myocardial infarction" *Cardiovasc. Res.* 28:1251-7, 1994; each of which is incorporated herein by reference). The fact that the increase in the non-mechanical cardiac work or PE (Table 1) was attenuated after ASM transplantation suggests a benefit to the mechanoenergetics of the heart. Such a benefit may allow for better cardiac performance overtime and this is supported by the fact that ASM animals had no further deterioration in their $E_{es}$ over the six weeks and that given more time this may have proven to be significant between groups. Studies are currently underway to evaluate whether improvements in cardiac function may be demonstrated at longer time points or after transplantation of a greater number of ASM cells.

Study Limitations

The animal model used in the present study approximates clinical ischemic HF in etiology, degree of pathology and coronary anatomy (Sabbah et al. "A canine model of chronic heart failure produced by multiple sequential coronary microembolizations" *Am. J. Physiol.* 260:H11379-84, 1991; Pfeffer et al. "Ventricular remodeling after myocardial infarction. Experimental observations and clinical implications" *Circulation* 81:1161-72, 1990; Menasche, "Myoblast-based cell transplantation" *Heart Failure Reviews* 8:221-27, 2003; each of which is incorporated herein by reference). Microembolization does not fully model the phenomenon of myocardial infarction leading to ischemic HF in all patients, particularly those patients who suffer a single large infarct. Moreover, this model greatly accelerates the disease progression typical for chronic ischemic HF (Pfeffer et al. "Ventricular remodeling after myocardial infarction. Experimental observations and clinical implications" *Circulation* 81: 1161-72, 1990; Pfeffer, "Left ventricular remodeling after acute myocardial infarction" *Annu. Rev. Med.* 46:455-66, 1995; each of which is incorporated herein by reference).

Each animal undervent the same number and types of procedures as well as being subjected to the same hemodynamic criteria for determination of HF. Differences found in the present study could have resulted based on the timing of instrumentation (and ASM injection) between the groups. The fact that attenuated dilatation was observed and correlated only in the SA dimension in HF+ASM animals, while LA dilatation was nearly identical between the HF control and ASM groups, further support that differences seen between groups were less dependent upon procedural order than on myoblast injection.

Segmental and/or regional function as measured by sonomicrometry may have not adequately documented function in the exact area of ASM engraftment due to the variability of ASM survival; however, myoblast injection was specifically targeted to and was found in the immediate vicinity of the sonomicrometry crystals at 6 weeks. If regional instrumentation failed to reveal functional benefit after ASM injection, then indices such as ESPVR ($E_{es}$) and PRSW ($M_w$) should have remained sensitive to changes in LV volume in relation to chamber pressures to account for the impact of ASM injection. As previously recognized, the method described by Abercrombie ("Estimation of nuclear population from microtome sections" *Ant. Rec.* 94:239-47, 1946; incorporated herein by reference) is a standardized approach to quantify cell numbers. It is a best estimate for the number of cells surviving, but sampling error is its major limitation. Lastly, the lack of observed benefit to LV function after ASM injection may be related to the limited period of study (Ghostine et al. "Long-term efficacy of myoblast transplantation on regional structure and function after myocardial infarction" *Circulation* 106[suppl I]:I131-6, 2002; incorporated herein by reference).

Conclusions

The present study describes ASM transplantation in a clinically applicable large animal model of chronic ischemic HF free of concomitant interventions. Despite the apparent lack of direct functional impact on cardiac function, we were able to demonstrate a significant attenuation in LV dilatation after ASM transplantation. The attenuation in LV dilatation was exclusive to the short axis and was observed in a cell survival-dependent fashion. These observations suggest that ASM impact LV remodeling by a mechanism independent of cell-to-cell communication and/or direct functional improvements, but that ASM engraftment and alignment may play a role in such a mechanism.

Example 2

Safety and Feasibility of Percutaneous Autologous Skeletal Myoblast Transplantation in the Coil-Infarcted Swine Myocardium All experiments were conducted according to guidelines published in the "*Guide for the Care and Use of Laboratory Animals*" (DHHS publication number NIH 85-23, revised 1985) and Subchapter A of the Federal Animal Welfare Act written by the United States Department of Agriculture and in the spirit of FDA Good Lab Practices. The study protocol was approved by the Harrington Animal Care and Use Committee at Arizona Heart Hospital, *Phoenix*, Ariz., prior to the start of the study.

Materials and Methods

Animal Preparation:

Ten female Yorkshire swine between the ages of 3 and 6 months and weighing 91±25 lbs. underwent induced myocardial infarction. Three died during or shortly after induction of the myocardial infarction. One animal was used to evaluate short term retention and biodistribution of injected myoblasts, and six animals served as recipient animals for either ASM or transport medium only.

Immediately prior to inducing infarction, electrocardiography, echocardiography, cardiac output and index, and blood values were assessed, muscle biopsies were obtained and loop recorder devices were implanted (see below for more details on these procedures). Each animal was anesthetized with intramuscular (tiletamine hydrochloride and zolazepam hydrochloride; 500 mg), intubated, and mechanically ventilated with 2% isoflurane and 3-L/min oxygen. An 8-F arterial sheath was inserted into the right femoral artery using either percutaneous or cutdown technique, and selective left and right coronary angiography, left ventriculography and NOGA™ mapping were performed.

Concurrent with the femoral cutdown, a biopsy was taken from each of the six studied swine. Under sterile conditions, a 6-cm incision was made longitudinally along the right hind limb, and a 5-10 grams biopsy of the thigh muscle was removed with a sharp dissection technique. The incision was then closed in layers. The muscle biopsy was placed immediately in a Biopsy Transplantation medium on ice and sent to a cell culturing facility for myoblast expansion.

Following the muscle biopsies, an implantable loop recorder (ILR) was inserted in each swine. Using sterile technique, a single 2 cm incision was made along the left side of the spine just above the heart level. The wound was dissected to the fascia, and an approximated 4×2 cm subcutaneous pocket was formed over the muscle. The event monitor was placed subcutaneously, and the electrocardiogram (ECG) signal quality and amplitude were verified. Wound closure was performed in a conventional fashion.

Infarction Model:

Immediately following ILR implantation and left heart catheterization, an anterior infarction was induced in each swine by coil embolization using either a 2×10 mm complex helical or a 3×23 mm diamond shape Vortx coil (Boston Scientific/Target, Natick, Mass.) to the distal left anterior descending (LAD) artery. Coronary occlusion occurred in an average of 16 minutes after coil deployment, as demonstrated by coronary angiography and ECG showing ST elevation in $V_1$-$V_3$ a few minutes after occlusion of the left anterior descending artery. The femoral artery was closed with either an Angio-Seal vascular closure device or using sutures, and the animals were recovered per standard operating procedures. Significant ventricular arrhythmias were treated with a 2% intravenous lidocaine bolus and electrical cardioversion. Post-procedural discomfort was treated with intramuscular butorphanol tartrate (Dolbrex, 1.0 mL).

Expansion of Myoblasts:

The autologous skeletal myoblasts were isolated by fine mincing of the muscle tissue followed by a three step enzymatic digestion containing a 0.5 mg/mL trypsin and 0.5 mg/mL collagenase. Cell released in each step were washed and plated on gelatin coated dishes. The cells were expanded over two passages in a growth medium (GM) composed of SkBM® (Skeletal Muscle Basal Medium, Cambrex Corporation, East Rutherfors, N.J.) supplemented with 15% (vol/vol) fetal bovine serum (Hyclone, Logan, Utah), 10 ng/mL rhEGF (Cambrex), 3.9 µg/mL dexamethasone (American Reagent Lab, Shirley, N.Y.), and 50 µg/mL gentamicin (Gibco/Invitrogen Corp, Carlsbad, Calif.). The cells were maintained at <70% density to prevent spontaneous cell fusion, and were harvested by trypsin/EDTA digestion and cryopreserved. Approximately 10% of the culture was labeled with bromodeoxyuridine (BrdU) during the last 24 hours of culture in order to facilitate identification of engrafted cells using BrdU-specific immunohistochemistry.

In preparation for cell injection, the frozen myoblasts were thawed and washed twice in GM and twice in Transplantation Medium. Finally, the cells were brought to the proper cell density, into 1 mL syringes and shipped either on ice or cold packs to the animal study facility.

To label cells with iridium, forty million cells from the animal were mixed with $13.4 \times 10^{10}$ iridium particles (0.3 µm diameter; supplied by BioPhysics Assay Laboratory, Worcester, Mass.) and incubated for 2.5 hrs at 37° C. to foster internalization of iridium by the myoblasts. Non-internalized particles were removed by washing the cells six times in growth medium. The remaining labeled cells were mixed with unlabelled myoblasts to formulate the final cell product in transplantation medium and loaded into 1 cc syringes. Aliquots of the final cell product were retained so that a standard curve could be generated (see below).

Characterization of Cell Population:

Cells were analyzed for viability, sterility, purity, and potency. Viability was assessed using trypan blue, and sterility was measured using a membrane filtration method and LAL (Limulus Amebocyte Lysate) Gel clot assay to detect endotoxins. Cell purity was determined by FACS (Fluorescence Activated Cell Sorting) using a primary antibody against myoblast-specific α7-integrin (H36 provided by Dr. Kaufman, University of Illinois). Myoblast potency was assessed using a fusion assay performed by switching confluent myoblast cultures to fusion media. Under these conditions, myoblasts fuse and form multinucleated myotubes. Contaminating fibroblasts do not have this property and remain as single cells.

At the time of final formulation in myoblast transplantation media, the cell viabilities were between 60% and 96% (see Table 4). Upon receipt of the myoblasts at the animal study site, the viabilities had decreased. The purity of the cell preparations ranged from 30% to 62%, with contaminating cells possibly being fibroblasts. All transplanted cells passed USP filtration sterility and endotoxin LAL testing.

Autologous Myoblast Transplantation:

Thirty days after infarction, autologous skeletal myoblasts were transplanted into each of the four treatment swine. Each animal was anesthetized as described above. An 8-F arterial sheath was inserted into the left femoral artery using a cut-down technique and myocardial assessments were repeated.

Percutaneous autologous skeletal myoblast transplantation was performed using an 8-F arterial sheath to advance an endovascular injection catheter (Biosense Intramyocardial Injection Device) through either the right or left femoral artery. A 3-D unipolar voltage map (NOGA™) was used to determine the area of infarction and to guide the needle-injection catheter. An average of 137 points were used to map the left ventricule, and a mean unipolar voltage of 7.8±1.5 mV (bipolar: 2.3±0.4 mV) was used to detect infarcted areas. The catheter used was either a B or C. The injection needle was measured in the straight and curved positions (90 degrees) and adjusted to extend 3 to 5.5 mm into the infarcted region of the endocardium depending on the wall thickness measured by echocardiography. Penetration was verified by either fluoroscopy, ST elevations, or premature ventricular contractions during needle advancement.

Immediately prior to injection, each syringe was warmed to room temperature and inverted several times to ensure a homogeneous cell suspension. The temperature was assessed by touch and homogeneity was assessed visually. The suspended cells were injected into the center and peripheral edges of the infarcted region of the myocardium. Group 2 animals received $\sim300 \times 10^6$ cells in 19 injections of 100 µL each. Group 3 animals received $\sim600 \times 10^6$ cells in 31 to 39 injections of between 100 and 150 µL. Group 1 animals (controls) were injected with myoblast transplantation media using similar numbers of injections and injection volumes. Table 4 describes dosing characteristics in detail. After the injections were complete, the femoral artery was closed with either an Angio-Seal vascular closure device or sutures, and the animals were recovered.

Quantitation of Distribution of Iridium-Labeled ASM

Two hours after the final injection, the animal injected with iridium labeled ASM was sacrificed and the heart, brain, kidneys, liver, lungs and spleen were weighed. The anterior, lateral, inferior and septal regions of the left ventricle were cut into eight equal segments (two vertical segments for each region, and 5-9 gm of each organ was removed for analysis. All tissue samples and labeled cell standards were placed in vials and dried overnight at 70° C.

The resulting dried samples were sent to BioPhysics Assay Laboratory for analysis involving two steps: activation and detection. During activation, the samples were exposed to high-energy neutrons allowing the iridium atoms in the cells to capture incident neutrons. The unstable radioactive products of the neutron flux were then allowed to decay for two days to reduce background interference. During the detection phase, the samples were placed in a high-resolution gamma-detection monitor that measured the energy level and the number of gamma particles emitted. A standard curve generated from samples containing known numbers of iridium-labeled cells was used to convert the gamma particle emission for each tissue sample to the number of retained iridium-labeled cells. To calculate the total number of labeled cells within each whole organ (other than the heart), the value for each tissue sample was multiplied by the weight of the organ divided by the sample tissue weight.

Safety Assessments:

Safety was evaluated by animal survival, well-being, heart rhythm, blood tests and adverse events. Well-being and survival were continuously monitored and recorded during the 90-day study period. Heart rhythm was monitored using a standard 12-lead electrocardiogram, obtained in a resting, supine position at selected time-points, and by an implantable loop recorder (ILR). The ILR used was the Medtronic Reveal® Plus 9526 (Medtronic, Minneapolis, Minn.), a single-use programmable device designed to continuously (i.e., looping) record a subcutaneous electrocardiogram during arrhythmic events. The ILR was activated during, and 24 hours following myocardial infarction and transplant. Additional interrogations were performed 3 times per week for 2 weeks after each procedure and weekly between transplant and harvest. Each device was programmed as follows: Storage mode—13 auto-activated events for 42 minutes to detect bradycardia<30 bpm, tachycardia>230 bpm, asystole>3 seconds for 16 consecutive beats. All ILR devices were set for a maximum gain of 8 (±0.2) mV and sensitivity was adjusted between 10 and 13 to achieve optimal sensing.

Hematology and Chemistry:

(see Table 3) Specimens were drawn at each intervention, after the animals were fasted overnight. Blood was collected from the femoral access under anesthesia type. Sodium EDTA was used as the anticoagulant for hematology tests. Samples for clinical chemistry tests were collected without anticoagulant.

TABLE 3

Laboratory Tests performed on Swine Blood Samples

| Hematology | hemoglobin |
|---|---|
| | platelet count |
| | hematocrit |
| | white blood cell count (leukocyte), and red blood cell count (erythrocyte) |
| | differential blood cell count |
| | blood cell morphology |
| Chemistry | glucose |
| | sodium, calcium, potassium, and chloride |
| | uric acid |
| | total bilirubin |
| | urea nitrogen |
| | creatine and creatine kinase |
| | total protein |
| | albumin, globulin, and albumin/globulin ratio |
| | cholesterol |
| | triglycerides |
| | inorganic phosphorous |
| | alkaline phosphatase |
| | alanine aminotransferase |
| | gamma glutamyltransferase |
| | aspartate aminotransferase |

Myocardial Function Assessment:

Functional assessment of the hearts was performed at selected time points to detect and compare the effects of cell transplantation in the treatment groups to controls.

Ejection fraction and ventricular wall thickness were assessed using a standard resting echocardiogram (ECHO). The ECHO was 2-dimensional and performed in the parasternal long and short axis views, four, two and long axis apical and subcostal four and short axis views. ECHO results were interpreted in a blinded fashion by an experienced cardiologist. Additional ejection fraction assessments were made by ventriculography (LV gram). Coronary arteries were visualized for patency through coronary angiography during left heart catheterization using the right and left anterior oblique projections, and were interpreted by the investigator. Cardiac index was assessed by non-invasive impedance cardiography (ICG) using a Bio-Z device (Cardio Dynamics International Corporation, San Diego, Calif.). Four ICG sensors were attached to each animal (one on both sides of the neck and torso), and a correction factor of 1.48 was used to adjust the values for pig chest anatomy (Broomhead et al., *Br. J. Anesth.* 78:323-325, 1997; incorporated herein by reference).

Three-dimensional electromechanical mapping was performed using the NOGA Biosense Navigational System (Biosense Webster, Diamond Bar, Calif.) via a 7-F NAVI-STAR™ catheter advanced through the 8-F sheath into the left ventricle. This navigational system uses a low-intensity magnetic field energy and sensor tipped catheters to local catheter position in 3-dimensional space. Coupled with electromechanical mapping, this permits construction of a 3-D image of the left ventricle (LV), which identifies areas of the healthy/normal, ischemia and infarction of the ventricle (Kornowski et al., *Circulation* 98:1116-1124, 1998; incorporated herein by reference). These maps included unipolar (UP) and bipolar (BP) voltage maps. A number and color scales to indicate the voltage in each area of the myocardium were assigned by the computer.

The Biosense injection Catheter is a multi-electrode, percutaneous catheter with a deflectable tip and injection needle designed to inject agents into the myocardium. The tip of the Injection Catheter is equipped with a Biosense location sensor and a retractable, hollow 27-gauge needle for fluid delivery. The injection site is indicated in real-time on the left ventricle map, allowing for precise distribution of the injections. Local electrical signals are obtained to minimize catheter-tip trauma.

Histology:

Histological analysis was performed on all hearts from the treatment and control group animals following harvest at day 90 of the study. The hearts were weighed and preserved in 10% neutral-buffered formalin and shipped at room temperature to GenVec for histological analysis. The infarcted portion of each heart was embedded in paraffin, sectioned and mounted on slides, which were stained to identify cellular transplantation engraftment and possible inflammatory reaction to the procedure. Histological stains included Hematocylin & Eosin, and Trichrome. Immunohistochemical stains included skeletal muscle-specific myosin heavy chain (MY32), and immunoreactivity to bromodeoxyuridine (BrdU).

Statistical Analysis:

Continuous variables among the groups were compared using the student t-test, with a p value of <0.05 considered significant. Relative percent change was calculated as difference between before and after values divided by baseline value.

Preliminary Experiments

Feasibility of Percutaneous Injections:

The feasibility of percutaneous catheter injection into both damaged and normal myocardium was initially evaluated in two pigs. Two different catheters were used to inject methylene blue or contrast dye into a normal swine and an infarcted swine myocardium on separated occasions. Prior to dye injection, an angiogram was performed to precisely position the catheter at the apex of the heart in the region of myocardial infarction. This preliminary experiment showed that it is possible to target specific regions of the heart for myoblast delivery.

Biocompatibility of the Injection Catheter:

Prior to initiating implantation studies using the Myo-Star™ Intramyocardial Injection Device (BioSense-Webster, Diamond Bar, Calif.), preliminary biocompatibility studies were performed. The experiment was also designed to verify microscopically the presence or absence of residue, which might have been expulsed from the catheter itself during cell passage. Myoblasts were supplied by GenVec on the day of the experiment in pre-labeled syringes at the following concentrations: 10, 30, 50, 70, and 100×10$^6$ cells/mL. The volumes of cell concentrations were 0.44, 0.44, 0.28, 0.45, and 0.40 mL, respectively. Cell viability was determined using trypan blue stain (0.4%, Gibco) before and after cell passage. The microscopic visual assessment for residue was performed at pre-catheterization, flush of catheter, and post-catheterization time points by using a light microscope at a 20× magnification. Digital photographs were take to document any residue that may have accumulated during the experiment.

Similar to a myogenic cell line (Oron et al. "Technical delivery of myogenic cells through an endocardial injection catheter for myocardial cell implantation" *Int. J. Cariovasc. Intervent.* 3:227-230, 2000; incorporated herein by reference), the data showed no significant alteration in cell viability after passing through the catheter at a range of cell concentrations from $10 \times 10^6$ to $100 \times 10^6$ cells/ml, suggesting that no adverse effects on cell viability take place when using the Biosense catheter. Furthermore, no difference was observed microscopically in the debris pre, flush, or post-catheterization at all dose concentrations.

| Cell Concentration | Injection Rate | % Viability Pre-Injection | % Viability Post-Injection |
|---|---|---|---|
| $10 \times 10^6$ | 0.5 ml/min | 91% | 90% |
| $30 \times 10^6$ | 0.5 ml/min | 93% | 92% |
| $50 \times 10^6$ | 0.4 ml/min | 82% | 87% |
| $70 \times 10^6$ | 1.0 ml/min | 85% | 94% |
| $100 \times 10^6$ | 0.7 ml/min | 83% | 86% |

Biosense Catheter Delivery of Myoblasts in the Infarcted Pig Myocardium:

The catheter delivery method previously described was used to inject myoblasts in the heart. Biopsies from the thigh muscle (approximately 5 grams) of 3 pigs were removed and shipped for myoblast culturing. Approximately 3 to 4 weeks post-biopsy, the cells were received for injection. Two myoblast transplants were performed using the Biosense NOGA mapping and injection. An autologous transplant was completed on one swine and a second received an allogeneic myoblast transplant in the absence of immunosuppression.

Figure 6:
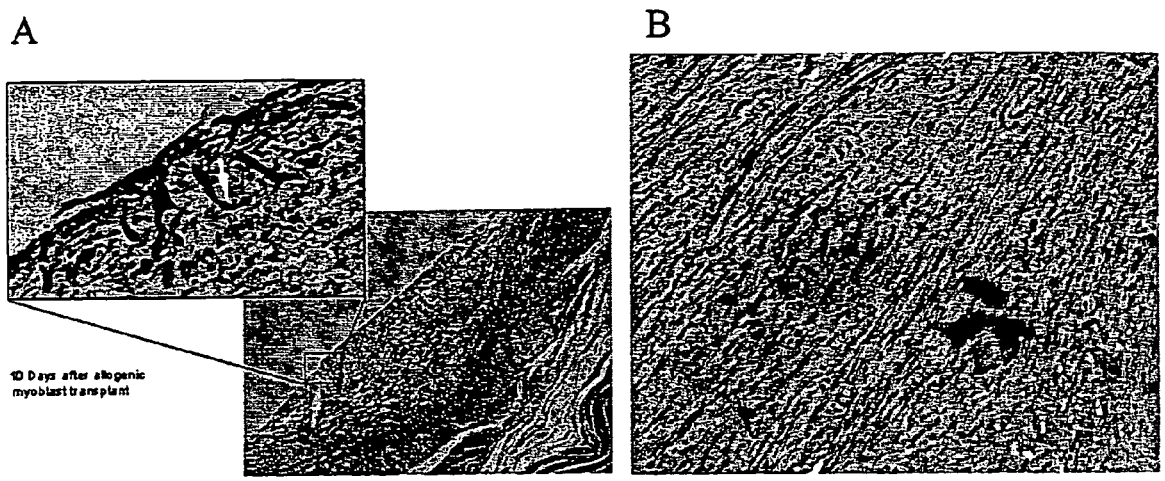
FIG. 6 shows Masson's trichrome histology of engrafted myoblasts. A) Low power (10x) view (right) of infarcted myocardium after myoblast injection. The area in the lower right hand corner is normal myocardium that stains red. The blue stained area is indicative of the fibrotic cells found in the scarred infarcted area. The red stippled area on the endocardial surface (arrow) contains proliferating myoblasts that are better appreciated in the high-power view (upper left; H&E, original magnification 200x). B) The myoblasts are forming multinucleated myotubes.

Penetration into the scar area was verified by ST elevations and by premature ventricular contractions during the needle advancement. Nine injections of 0.1 mL at $5.6 \times 10^4$ cells/mL (autologous injection) and 25 injections of 0.1 mL at $200 \times 10^6$ cells/mL (allogeneic) were performed, respectively on the two pigs. The injection sites were delineated on the electromechanical map. Successful transplantation was observed upon myocardial harvest performed at 10 days (allogeneic) and three months (autologous) (see FIG. 6) (Nib et al. *J. Envasc. Ther.* 9:313-319, 2002; incorporated herein by reference)

Results

Figure 5:
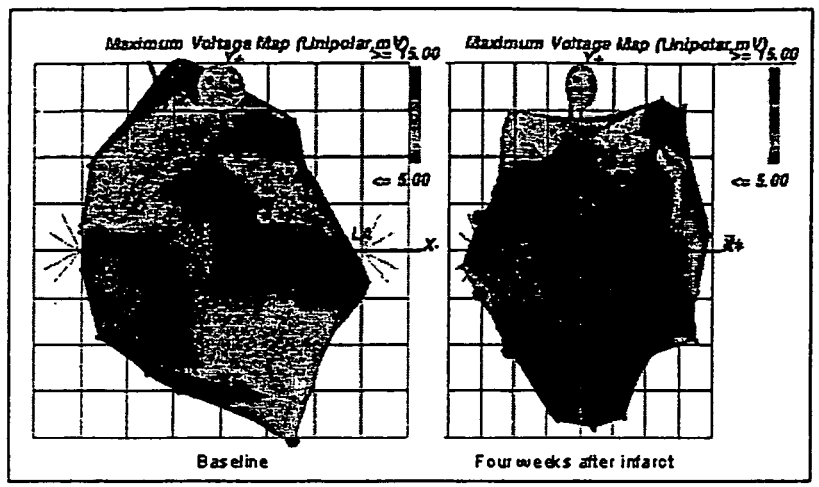
FIG. 5 is a picture from a NOGA Biosense navigational system. A 3-dimensional electromechanical (voltage) mapping pre- and post-shortening in the anteroapical and anteroseptal wall. Color coding for NOGA map is represented by a rainbow pattern of purple (>15.00 mV) to red (<=5.00 mV) from high to low voltage.

Bioretention and Distribution of Myoblasts in a Porcine Model:

The area of infarction is thinner than a healthy myocardial wall. Although the delivery of dyes was successful, catheter delivery of cells to damaged regions of the heart might present different challenge compared to the normal, thicker wall. A myocardial infarction was induced in a pig by placing a platinum coil in the left anterior descending artery. Just prior to the transplantation, the myoblasts were labeled by internalization of iridium particles. One month after myocardial infarction, the iridium labeled myoblasts were transplanted using a Biosense catheter guided by 3-D NOGA™ mapping (see FIG. 5). Two hours post-transplantation, the pig was sacrificed, and the heart, brain, spleen, liver, and both kidneys and lungs were harvested. The organs were evaluated for myoblast retention by exposing the tissues to a high-energy neutron source. Gamma particles emitted from the excited iridium were counted as an indirect quantitative measurement of myoblast localization. Approximately 4.1% of the myoblasts were found in the infarcted zone that had received injections. Approximately 5% of the myoblasts were found in the lungs. Less than 0.1% was found in the spleen, and no myoblasts were detected in the brain, liver, or kidney.

These data show that cells can be accurately targeted into specific regions (thin walled infarction area) of the myocardium using the Biosense Intramyocardial Injection Device. Overall retention in the sites of injection is approximately 4% using this mode of delivery. Cells which did not remain in the heart wall, presumably either leaked back into the ventricle through the needle track, or were injected into the cardiac venous system and traveled into the lungs. Even though a large majority of the injected cells were not accounted for, they were not detected in appreciable amounts in the brain, kidney, liver or spleen thus suggesting that the cells may dissipate throughout the animal at levels too low to detect.

Safety and Feasibility of a Autologous Skeletal Myoblast Transplantation using the Biosense Injection Catheter System:

Table 4 summarizes the results of the characterization of the autologous skeletal myoblasts. At the time of final formulation in Myoblast Transplantation Media, the cell viabilities were between 60 and 96%, and the viabilities were observed to have decreased when received at the animal study facility. All transplanted cells passed a USP filtration sterility and endotoxin LAL testing.

TABLE 4

Dosing of Control and Cell Transplanted Animals

| Group | Pig # | # injected cells | Cell Viability (%) At Shipment | Prior to Transplant | % Purity* | Number of Inj. | Vol/Inj (ml) | Total Vol Inj. (ml) |
|---|---|---|---|---|---|---|---|---|
| Control | 03 | Medium | N/A | N/A | N/A | 20 | 0.15 | 3.0 |
| Control | 08 | Medium | N/A | N/A | N/A | 28 | 0.10 | 2.8 |
| 1 | 06 | $233 \times 10^6$ | 77 | 54 | ND | 19 | 0.10 | 1.9 |
| 1 | 07 | $302 \times 10^6$ | 96 | 79 | 30 | 19 | 0.10 | 1.9 |
| 2 | 09 | $595 \times 10^6$ | 89 | 60 | 35 | 39 | 0.15 | 5.9 |
| 2 | 11 | $756 \times 10^6$ | 81 | 73 | 62 | 31 | 0.15 | 4.7 |

*Percent α7 integrin immunostaining by FACS
N/A—not applicable
ND—not done

Control animals (Group 1) were injected with Myoblast Transplantation Media using similar numbers of injection and injection volumes to corresponding treated animals in Groups 2 and 3. Group 2 animals were injected with approximately $300\times10^6$ cells in 19 injections of 100 µL each. Group 3 animals were injected with approximately $600\times10^6$ cells in 31 to 39 injections of between 100 and 150 µL each. Table 4 describes dosing characteristics in detail.

In all groups, there were no complications or deaths related to the catheter-based delivery of autologous skeletal myoblast. Heart rhythm was monitored using a standard 12-lead ECG, obtained in a resting, supine position at selected timepoints, and by an implantable loop recorder (ILR). The ILR was activated during, and 24 hours following, MI and transplant. Additional interrogations were performed 3 times/week for 2 weeks after each procedure and weekly between transplant and harvest. The ILR recorded one episode of non-sustained ventricular tachycardia and 2 episodes of sinus tachycardia, all recorded prior to transplantation. There were no arrhythmias were recorded by ILR in any group during the 60-day period following ASMT (see Table 5).

Table 5

Results from Loop Recorder.

| Group | Pig No. | No. of Interrogations | Arrhythmia Pre-Transplant | Arrhythmia Post-Transplant |
|---|---|---|---|---|
| Control, Group 1 | 1-001-03 | 23 | 1-NSVT post M1 | 0 |
|  | 1-001-08 | 25 | 0 | 0 |
| Treatment, Group 2 | 1-001-06 | 23 | 0 | 0 |
|  | 1-001-07 | 21 | 2-ST | 0 |
| Treatment, Group 3 | 1-001-09 | 22 | 0 | 0 |
|  | 1-001-11 | 21 | 0 | 0 |

NSVT = non-sustained ventricular tachycardia, and
ST = sinus tachycardia.

Myocardial Function.

Functional assessments of the hearts were performed to detect and compare changes in viability and function that may have occurred in the treatment groups compared to controls. At the time of transplant (baseline), no significant differences in EF by ECHO, EF by LV gram, cardiac index by Bio-Z, left ventricular unipolar voltage (LVUPV) by NOGA, and apical unipolar voltage (APUPV) by NOGA were found between the treatment and control groups.

At sacrifice, a consistent trend toward improved cardiac function was seen in the treatment groups relative to controls (Table 6). Given that there were no obvious differences between improvements in cardiac function between animals which were injected with 300 million versus 600 million ASM, the data from both treatment groups were pooled for analysis. By blinded echocardiographic assessment, the treated animals exhibited a 15% improvement in EF by ECHO versus an −10% deterioration in control animals, and a 2% decreases in EF by LV gram versus a 12% deterioration in control animals. Finally, the mean APUPV improved by 23% in treated animals but declined 4% in control animals.

TABLE 6

Cardiac Functional Parameters at the Time of ASMT (Baseline) and 60 Days Later (Sacrifice)

| | Ejection Fraction | | | | |
|---|---|---|---|---|---|
| | ECHO | LV gram | Cardiac Index | LVUVP | APUPV |
| Control: Group 1 (n = 2) | | | | | |
| Baseline | 49 | 43 | 0.85 | 7.8 | 7.5 |
| Sacrifice | 44 | 38 | 0.65 | 9.3 | 7.2 |
| % Change | −10 | −12 | −24 | 19 | −4 |
| Treated: Group 2 & 3 (n = 4) | | | | | |
| Baseline | 46 | 42 | 0.95 | 7.9 | 7.7 |
| Sacrifice | 53 | 41 | 0.83 | 9.3 | 9.5 |
| % Change | 15 | −2 | −13 | 18 | 23 |

Laboratory Chemistry Data:

No significant changes in complete blood count, Platelet, white blood cell differential, blood urea nitrogen, Electrolyte, Bicarbonate, Anion gap, Creatinine, LFT, alkaline phosphatase, creatine, B-type Natriuretic peptide, calcium and Phosphate, uric acid, cholesterol and triglyceride levels measured at baseline, transplant (1 month post-myocardial infarction) and harvest (2 months post-transplant). In addition, no significant differences in hematology and blood chemistry were seen between the two treatment groups and controls at any selected time point.

Histology:

Histological analysis of sections taken through the anterior left ventricular wall of each treatment pig showed lack of cell survival 60 days after implantation. No injected myoblasts or more mature multinucleated myotubes were detected using H&E and trichrome stains, or myoblast specific myosin heavy-chain immunostaining (MY-32). Morphologic evaluation with H&E and trichrome stains was not sufficiently sensitive for the 2 definitive determination of myoblast presence or absence. Also, immunostaining for nuclear BrdU was negative on all animals. Lesions in graft-recipient pigs were not more severe or quantitatively different than those in the control animals.

Taken together these data indicate that percutaneous, catheter-based transplantation of autologous skeletal myoblasts does not have a deleterious effect on the general well-being of the recipient animals or the infarcted swine heart muscle. In addition, the trend toward improved myocardial function seen in the two treatment groups compared to controls not only supports the safety findings, but also indicates that catheter-based delivery is feasible and results in greater overall heart function.

Discussion

Experimentally, myoblasts have been delivered into the injured heart using a number of methods, including intravascular infusion into the coronary circulation (Taylor et al., *Proc. Assoc. Am. Physicians* 109:245-253, 1997; incorporated herein by reference), direct injection of myoblasts into the injured myocardium (Taylor et al., *Proc. Assoc. Am. Physicians* 109:245-253, 1997; Dib et al. *Circulation* 108(suppl 17):IV-623, 2003; each of which is incorporated herein by reference) and, most recently, by catheter-based endoventricular delivery (Dib et al., *J. Endovasc. Ther.* 9:313-319, 2000; incorporated herein by reference). Catheter-based delivery is more challenging than direct injection since the myocardial wall is thinner than in healing tissue. Thus, the safety of using a needled injection catheter to deliver the cells to a thin wall was examined and the risk of perforation and cell leakage were assessed.

A 4.1% bioretention rate of iridium-labeled autologous skeletal myoblasts in infarcted myocardium was obtained by studying one of the treated swine. It is known from human trials that myoblasts transplanted by epicardial delivery survive and form myotubes and myofibrils (Menashe et al., *J. Am. Coll. Cardiol.* 41:1078-1083, 2003; incorporated herein by reference). Additionally, histological analysis of explanted hearts from LVAD patients five months post-transplant demonstrated expression of skeletal muscle slow twitch myosin, suggesting that the graft is able to survive in a foreign environment (Pagani et al., *J. Am. Coll. Cardiol.* 41 879-888, 2003; incorporated herein by reference).

In the safety and feasibility study presented herein, there were no complications related to the transplant procedure using a percutaneous catheter delivery approach. Interrogation of a surgically implanted loop recorder revealed no arrhythmias when up to 600 million cells in a total volume of 5.85 mL were injected. There were also no cardiac enzymes elevated at 2 months, which might indicate inflammatory or tumogenicity processes. However, complications were not observed that occurred after myocardial infarction and prior to the cell transplant procedure; one pig did not survive the myocardial infarction, one pig had sustained VT and two had sinus tachycardia.

There was a trend toward improvement in heart function by echocardiography, left ventriculography, and conductive output, despite negative histochemical staining with MY-32. This paradoxal finding suggests that the improvement in the treated groups might be due to recruitment of other cell types of the area of myocardial infarction, nascent angiogenesis or prevention of further apoptosis. It also creates a notion that longevity of the transplanted myoblast may not be crucial to the long-term improvement in myocardial function.

One of the limitations of the present study was that while the echocardiography results were evaluated in a blind fashion, the left ventriculography results were not. A blinded evaluation of this assessment may have increased the accuracy of the results.

It is known from a large number of animal and clinical studies in species other than pigs (rats (Jain et al., *Circulation* 103:1920, 2001; incorporated herein by reference), rabbits (Taylor, *Nature Med.* 4:929, 1998), sheep (Ghostine, *Circulation* 106[suppl I]:I-131-I-136, 2002), humans (Hagege, *Lancet* 361:492, 2003; Pagani et al. "Autologous skeletal myoblasts transplanted to ischemia-damaged myocardium in humans" *J. Am. Coll. Cardiol.* 41:879-888, 2003; each of which is incorporated herein by reference) that myoblasts transplanted by epicardial delivery survive and form myotubes and myofibrils, suggesting that grafted myoblasts are able to survive in a foreign environment. We currently speculate that porcine myoblasts have a unique property which does not allow them to survive long-term in the normal or infarcted myocardium. This conclusion is based on unpublished findings in other studies using epicardially injected porcine myoblasts which did not show ASM survival beyond a few days after implantation (data not shown). In the literature, there are references to short term myoblasts transplant studies in the porcine heart (Brasselet et al. "The coronary sinus: A safe and effective route for percutaneous myoblast transplantation" *J. Am. Coll. Cardiol.* 41:67A-68A, 2003; Chazaud, *Cardiovasc. Res.* 58:444-450, 2003; each of which is incorporated herein by reference), but no long-term studies describing ASM survival.

In summary, the data obtained indicate that delivery of autologous skeletal myoblasts via percutaneous endoventricular technique into a coil-infarcted swine myocardium may be done safely, without adverse events related to the procedure or toxicity to the cells. Furthermore, the present findings support previous studies that indicate that catheter-based delivery of autologous skeletal myoblasts is feasible and that the procedure leads to improved cardiac function.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A method of treating a patient with heart disease, the method comprising steps of: treating a patient suffering from heart disease using a left ventricular assist device; treating the patient using cellular cardiomyoplasty; and removing the left ventricular assist device from the heart, without orthotopic cardiac transplantation, when measurement of ventricular volume shows at least a 10% improvement.

2. The method of claim 1, wherein the step of treating the patient using cellular cardiomyoplasty comprises administering cells to the heart of the patient.

3. The method of claim 2, wherein the cells are selected from the group consisting of skeletal myoblasts, fetal cardiomyocytes, embryonic stem cells, and bone marrow stem cells.

4. The method of claim 2, wherein the cells are autologous skeletal myoblasts.

5. The method of claim 1, wherein the step of treating the patient using cellular cardiomyoplasty is performed before or while the patient is being treated using a left ventricular assist device.

6. The method of claim 1, wherein the patient is suffering from acute heart disease.

7. The method of claim 1, wherein the patient is suffering from chronic heart disease.

8. The method of claim 1, wherein the heart disease is selected from the group consisting of coronary artery disease, valvular heart disease, myocarditis, heart failure, dilated ischemic heart failure, congestive heart failure, cardiomyopathy, dilated cardiomyopathy, myocardial infarction.

9. The method of claim 1, wherein the number of cells administered ranges from $1 \times 10^6$ to $10 \times 10^9$ cells.

10. The method of claim 1, wherein the number of cells administered ranges from $1 \times 10^7$ to $1 \times 10^9$ cells.

11. The method of claim 1, wherein the cells are greater than 90% viable.

12. The method of claim 1, wherein the cells are greater than 90% pure skeletal myoblasts.

13. The method of claim 1, wherein the cells are greater than 80% pure skeletal myoblasts.

14. The method of claim 1, wherein the step of treating the patient with a left ventricular assist device is terminated at least 1 week after the step of treating the patient with cellular cardiomyoplasty is performed.

15. The method of claim 1, wherein the step of treating the patient with a left ventricular assist device is terminated at least 4 weeks after the step of treating the patient with cellular cardiomyoplasty is performed.

16. The method of claim 1, wherein the step of treating the patient with a left ventricular assist device is terminated at least 8 weeks after the step of treating the patient with cellular cardiomyoplasty is performed.

17. The method of claim 1, wherein the step of treating the patient with a left ventricular assist device is terminated at least 6 months after the step of treating the patient with cellular cardiomyoplasty is performed.

18. The method of claim 1, wherein the step of treating the patient with a left ventricular assist device is terminated at least 12 months after the step of treating the patient with cellular cardiomyoplasty is performed.

19. The method of claim 1, wherein the step of treating the patient with a left ventricular assist device is terminated at least 18 months after the step of treating the patient with cellular cardiomyoplasty is performed.

20. The method of claim 1, wherein the step of treating the patient with a left ventricular assist device is terminated at least 24 months after the step of treating the patient with cellular cardiomyoplasty is performed.

\* \* \* \* \*